(12) United States Patent
Gilday

(10) Patent No.: US 7,612,077 B2
(45) Date of Patent: Nov. 3, 2009

(54) CRYSTALLINE FORMS OF THE ANTI-CANCER COMPOUND ZD1839

(75) Inventor: John Peter Gilday, Bristol (GB)

(73) Assignee: Astrazeneca AB, Sodertalje (SE)

( * ) Notice: Subject to any disclaimer, the term of this patent is extended or adjusted under 35 U.S.C. 154(b) by 809 days.

(21) Appl. No.: 10/505,690

(22) PCT Filed: Feb. 24, 2003

(86) PCT No.: PCT/GB03/00794

§ 371 (c)(1),
(2), (4) Date: May 23, 2005

(87) PCT Pub. No.: WO03/072108

PCT Pub. Date: Sep. 4, 2003

(65) Prior Publication Data

US 2005/0209229 A1  Sep. 22, 2005

(30) Foreign Application Priority Data

Feb. 26, 2002 (GB) ................. 0204392.5
May 30, 2002 (GB) ................. 0212462.6

(51) Int. Cl.
*A61K 31/517* (2006.01)
*C07D 239/94* (2006.01)
(52) U.S. Cl. .................. 514/258.1; 544/253
(58) Field of Classification Search ............ 544/253; 514/258.1
See application file for complete search history.

(56) References Cited

U.S. PATENT DOCUMENTS 5,457,105 A   10/1995   Barker
5,616,582 A   4/1997    Barker
5,770,599 A   6/1998    Gibson

FOREIGN PATENT DOCUMENTS

WO  96/33980       10/1996
WO  96/33980 A     10/1996
WO  WO-96/33980  * 10/1996
WO  01/76586 A1   10/2001
WO  03/072139 A1   9/2003

* cited by examiner

*Primary Examiner*—Joseph K McKane
*Assistant Examiner*—Janet L Coppins
(74) *Attorney, Agent, or Firm*—Morgan Lewis & Bockius LLP

(57) ABSTRACT

The invention concerns certain crystalline solvates and hydrates of the compound of the Formula (I) which is known inter alia by way of the code number ZD1839. In particular, the invention concerns a first solvate that occurs in the presence of methanol which is designated as Form 2 ZD1839 MeOH solvate, a second solvate that occurs in the presence of dimethyl sulphoxide which is designated as Form 3 ZD1839 DMSO solvate and a trihydrate that occurs in the presence of water which is designated Form 5 ZD1839 trihydrate. The invention further concerns processes for the preparation of these solvates and the trihydrate and for their conversion back to the compound ZD1839, pharmaceutical compositions containing them and their use in the manufacture of medicaments for use the production of an anti-proliferative effect in a warm-blooded animal such as man.

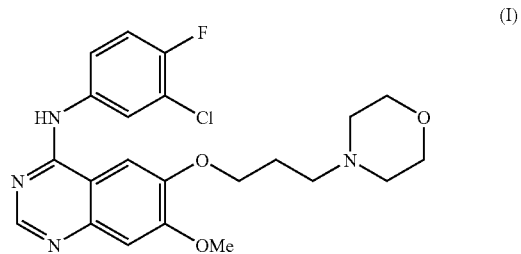

(I)

13 Claims, 6 Drawing Sheets

FIG 1/11 XRPD Pattern of Form 1 ZD1839 Polymorph

FIG 2/11 DSC & TGA scans for Form 1 ZD1839 Polymorph

FIG 3/11 DRIFT scan for Form 1 ZD1839 Polymorph

FIG 4/11 XRPD Pattern of Form 2 ZD1839 MeOH solvate

FIG 5/11 DSC & TGA scans for Form 2 ZD1839 MeOH solvate

FIG 6/11 DRIFT scan for Form 2 ZD1839 MeOH solvate

FIG 7/11  XRPD Pattern of Form 3 ZD1839 DMSO solvate

FIG 8/11  DSC & TGA scans for Form 3 ZD1839 DMSO solvate

FIG 9/11 DRIFT scan for Form 3 ZD1839 DMSO solvate

Figure 10/11 XRPD Pattern of Form 5 ZD1839 Trihydrate

Figure 11/11 DSC and TGA scans for Form 5 ZD1839 trihydrate

CRYSTALLINE FORMS OF THE ANTI-CANCER COMPOUND ZD1839

RELATED APPLICATIONS

This application is a U.S. National Phase Application of International Application No. PCT/GB03/00794, filed Feb. 24, 2003, which claims the benefit of foreign priority to UK Application No. 0204392.5, filed Feb. 26, 2002 and U.S. application Ser. No. 021246.6, filed May 30, 2002.

The present invention relates to particular crystalline forms of a pharmaceutical compound, to processes for their preparation, to their use in the purification of that pharmaceutical compound, to pharmaceutical compositions comprising them and to their use in therapy.

International Patent Application WO 96/33980 discloses within Example 1 the compound 4-(3'-chloro-4'-fluoroanilino)-7-methoxy-6-(3-morpholinopropoxy)quinazoline. That compound is an inhibitor of the epidermal growth factor receptor (EGFR) family of tyrosine kinase enzymes such as erbB1 and possesses anti-proliferative activity such as anti-cancer activity and, accordingly, is useful in methods of treatment of proliferative disease such as cancer in the human or animal body.

That compound has the structure of the Formula I

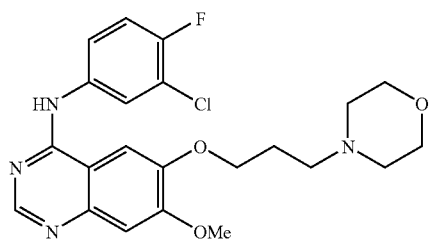

and is now known as Iressa (registered trade mark) and gefitinib (United States Adopted Name) and by way of the code number ZD1839 and Chemical Abstracts Registry Number 184475-35-2.

The subject matter of Example 1 of International Patent Application WO 96/33980 discloses the preparation of the compound of the Formula I which, after purification by column chromatography on silica using a 4:1 mixture of ethyl acetate and methanol as eluent and recrystallisation from toluene, is stated to have m.p. 119-120° C. The subject matter of Example 10 of that patent application discloses an alternative synthetic route to the compound of the Formula I that involves purification by column chromatography on silica using a 9:1 mixture of methylene chloride and methanol as eluent and recrystallisation from toluene. There is no specific disclosure in either of Examples 1 and 10 of International Patent Application WO 96/33980 whether the compound of the Formula I is crystalline or amorphous. Furthermore, there is no specific disclosure in those examples whether the compound may exist in a solvated form.

It is stated in International Patent Application WO 96/33980 that the quinazoline derivatives disclosed therein can exist in solvated as well as unsolvated forms such as, for example, hydrated forms and that the invention therein encompasses all such solvated forms which possess anti-proliferative activity. However, no particular hydrated forms are disclosed and no particular solvates are disclosed.

We have now found that certain forms of the compound of Formula I including certain solvates thereof are crystalline materials that possess advantageous properties.

A particular crystalline form of a compound may have physical properties that differ from those of any other crystalline or amorphous form and such properties may influence markedly the chemical and pharmaceutical processing of the compound, particularly when the compound is prepared or used on a commercial scale. For example, each crystal form of a compound may show differences in physical properties such as crystalline size and shape, melting point, density, hygroscopicity and stability. Such differences may alter the mechanical handling properties of the compound (such as the flow characteristics of the solid material) and the compression characteristics of the compound. Different crystalline forms of a compound may have different thermodynamic stabilities. In general, the more stable form, for example the more stable polymorphic form, is the more suitable physical form for formulation and processing on a commercial scale.

For example, problems could arise in the processing of a less stable form, for example a less stable polymorph. Compression forces such as those used in tabletting processes could convert some of a less stable form into a more stable form resulting in growth of crystals of the more stable form in the formulated product. This could be undersirable since any such crystallisation process could disrupt the integrity of the tablet resulting in a friable tablet of decreased tablet strength. In addition, if a variable mixture of two such forms were to be present, the dissolution rate and bioavailability of the active compound(s) could be variable as, for example, each form could have a different particle size. It is well known that particle size can affect the dissolution rate and bioavailability of a pharmaceutically-active compound. The quality of the product could therefore be affected undesirably.

Furthermore it is preferred that pharmaceutical compounds in the form of capsules or tablets are prepared using the most stable form, for example the most stable polymorph, and not a metastable phase or mixture of forms as there is a requirement to demonstrate to the appropriate regulatory authorities that the composition of the compound is controlled and stable. If a thermodynamically less stable form, for example a less stable polymorph, were resent alone or in admixture with a thermodynamically more stable form in a tablet, it would be very difficult to control the composition of the tablet, for example the polymorphic composition of the tablet, since the quantity of the more thermodynamically stable form could end to increase on storage.

Accordingly, these factors may have an impact on solid phase, tablet or capsule formulations of the compound and on suspension formulations thereof.

A study of the properties of the compound of the Formula I has been performed to discover whether polymorphism and/or solvate formation is possible. A wide range of recrystallisation solvents of various polarities was investigated. From most of these solvents, only a single non-solvated, crystalline form of the compound of the Formula I was obtained which is designated hereinafter as Form 1 ZD1839 polymorph. Two solvates were also identified as of interest. The first solvate occurred in the presence of methanol and this is designated hereinafter as Form 2 ZD1839 MeOH solvate and the second solvate occurred with dimethyl sulphoxide and this is designated hereinafter as Form 3 ZD1839 DMSO solvate. We have also found a trihydrate, designated hereinafter as form 5 ZD1839 trihydrate.

In particular, it has now been found that Form 3 ZD1839 DMSO solvate is crystalline and that, surprisingly, that form has advantageous properties.

Further, we have discovered that Form 3 ZD1839 DMSO solvate is unusual in that it possesses a crystalline physical form that is easily isolated and is also very stable. Moreover, this solvate may readily be prepared on a commercial scale at a high level of purity and in high yield. In addition this solvate may readily be converted into the compound of Formula I, in particular into the compound of Formula I in the form of Form 1 ZD1839 polymorph. Overall, the inclusion of the steps of DMSO solvate preparation, purification thereof and conversion back to the compound of Formula I is beneficial in terms of yield and purity of the compound of Formula I.

According to one aspect of the present invention there is provided a crystalline form of the compound of the Formula I substantially in the form of Form 3 ZD1839 DMSO solvate.

According to a further aspect of the present invention there is provided a crystalline form of the compound of the Formula I substantially in the form of Form 3 ZD1839 DMSO solvate and substantially free of any other ZD1839 solvate or any Form 1 ZD1839 polymorph.

When it is stated that the present invention relates to a crystalline form of the compound of the Formula I, the degree of crystallinity as determined by X-ray powder diffraction data is conveniently greater than about 60%, more conveniently greater than about 80%, preferably greater than about 90% and more preferably greater than about 95%. Most preferably, the degree of crystallinity as determined by X-ray powder diffraction data is greater than about 98%.

When it is stated that the present invention relates to Form 3 ZD1839 DMSO solvate, the molar ratio of ZD1839 to dimethyl sulphoxide solvent molecule is in the range 3:1 to 1:3, preferably in the range 2.1 to 1:2, more preferably about 1 equivalent of ZD1839 to about 1 equivalent of DMSO.

When it is stated that the present invention relates to a crystalline form of the compound of the Formula I substantially in the form of Form 3 ZD1839 DMSO solvate, this means that at least 80% of the compound of the Formula I is in the form of Form 3 ZD1839 DMSO solvate. Preferably at least 90% and, in particular, at least 95% of the compound of the Formula I is in the form of Form 3 ZD1839 DMSO solvate. More preferably at least 98% of the compound of the Formula I is in the form of Form 3 ZD1839 DMSO solvate.

When it is stated that the invention relates to Form 3 ZD1839 DMSO solvate substantially free of any other ZD1839 solvate or any Form 1 ZD1839 polymorph, this means that at least 80% of the compound of the Formula I is in the form of Form 3 ZD1839 DMSO solvate and less than 20% of the compound of the Formula I is in the form of any other ZD1839 solvate or any Form 1 ZD1839 polymorph. Preferably at least 90% and, in particular, at least 95% of the compound of the Formula I is in the form of Form 3 ZD1839 DMSO solvate.

Further, we have discovered that Form 2 ZD1839 MeOH solvate also possesses a crystalline physical form that is easily isolated and it is of sufficient stability readily to be prepared on a commercial scale at a high level of purity and in high yield. In addition this solvate may be converted into the compound of Formula I.

According to a further aspect of the present invention there is provided a crystalline form of the compound of the Formula I substantially in the form of Form 2 ZD1839 MeOH solvate.

According to a further aspect of the present invention there is provided a crystalline form of the compound of the Formula I substantially in the form of Form 2 ZD1839 MeOH solvate and substantially free of any other ZD1839 solvate or any Form 1 ZD1839 polymorph.

When it is stated that this aspect of the present invention relates to a crystalline form of the compound of the Formula I, the degree of crystallinity as determined by X-ray powder diffraction data is conveniently greater than about 60%, more conveniently greater than about 70%, preferably greater than about 80% and more preferably greater than about 90%. Most preferably, the degree of crystallinity as determined by X-ray powder diffraction data is greater than about 95%.

When it is stated that the present invention relates to Form 2 ZD1839 MeOH solvate, the molar ratio of ZD1839 to methanol solvent molecule is in the range 6:1 to 1:3, preferably in the range 4:1 to 1:2, more preferably about 2 equivalents of ZD1839 to about 1 equivalent of methanol, i.e. the material can be approximately a hemi-solvate.

When it is stated that the present invention relates to a crystalline form of the compound of the Formula I substantially in the form of Form 2 ZD1839 MeOH solvate, this means that at least 80% of the compound of the Formula I is in the form of Form 2 ZD1839 MeOH solvate. Preferably at least 90% and, in particular, at least 95% of the compound of the Formula I is in the form of Form 2 ZD1839 MeOH solvate. More preferably at least 98% of the compound of the Formula I is in the form of Form 2 ZD1839 MeOH solvate.

When it is stated that the invention relates to Form 2 ZD1839 MeOH solvate substantially free of any other ZD1839 solvate or any Form 1 ZD1839 polymorph, this means that at least 80% of the compound of the Formula I is in the form of Form 2 ZD1839 MeOH solvate and less than 20% of the compound of the Formula I is in the form of any other ZD1839 solvate or any Form 1 ZD1839 polymorph. Preferably at least 90% and, in particular, at least 95% of the compound of the Formula I is in the form of Form 2 ZD1839 MeOH solvate.

Certain other solvates of the compound of Formula I may be obtained but these do not possess crystalline physical forms that are both easily isolated and stable. For example, when the compound of Formula I was allowed to crystallise by the slow evaporation of a solvent system comprising a particular mixture of isopropanol and water, the crystalline solid obtained comprised an isopropanolate solvate that also carried two equivalents of water. However, for example, when the compound of Formula I was recrystallised in a solvent system comprising a mixture of isopropanol and water, under some conditions the crystalline solid obtained comprised not only Form 1 ZD1839 polymorph but also a further material which is believed to be a metastable anhydrate ZD1839 polymorphic form.

In contrast, from many solvents only a single non-solvated, crystalline form of the compound of the Formula I was obtained which is designated as Form 1 ZD1839 polymorph. We have discovered that Form 1 ZD1839 polymorph possesses a crystalline physical form that is easily isolated and is also highly stable such that this polymorph may readily be prepared on a commercial scale at a high level of purity and in high yield. There is therefore provided a crystalline form of the compound of the Formula I substantially in the form of Form 1 ZD1839 polymorph, preferably substantially free of any other polymorphic form of ZD1839 or of any ZD1839 solvate or hydrate.

Form 1 ZD1839 polymorph has a melting point in the range of about 194° C. to 198° C. it was not disclosed in International Patent Application WO 96/33980 that the compound of the Formula I could exist in a polymorphic form of m.p. about 195° C., nor was a process disclosed for preparing that polymorph substantially free of any other polymorphic form of ZD1839 or of any ZD1839 solvate. It was disclosed in International Patent Application WO 96/33980 that the compound 4-(3'-chloro-4'-fluoroanilino)-7-methoxy-6-(3-morpholinopropoxy)quinazoline, now known by way of the code number ZD1839, had m.p. 119-120° C. It is believed that the material obtained at that time may have been the metastable anhydrate polymorphic form of ZD1839.

When it is stated that a crystalline form of the compound of the Formula I in the form of Form 1 ZD1839 polymorph may be obtained, the degree of crystallinity as determined by X-ray powder diffraction data is conveniently greater than about 60%, more conveniently greater than about 70%, preferably greater than about 80% and more preferably greater than about 90%. Most preferably, the degree of crystallinity as determined by X-ray powder diffraction data is greater than about 95%.

When it is stated that a crystalline form of the compound of the Formula I may be obtained that is substantially in the form of Form 1 ZD1839 polymorph, this means that at least 80% of the compound of the Formula I is in the form of Form 1 ZD1839 polymorph. Preferably at least 90% and, in particular, at least 95% of the compound of the Formula I is in the form of Form 1 ZD1839 polymorph. More preferably at least 98% of the compound of the Formula I is in the form of Form 1 ZD1839 polymorph.

When it is stated that Form 1 ZD1839 polymorph may be obtained substantially free of any other polymorphic form of ZD1839 or of any ZD1839 solvate, this means that at least 80% of the compound of the Formula I is in the form of Form 1 ZD1839 polymorph. Preferably at least 90% and, in particular, at least 95% of the compound of the Formula I is in the form of Form 1 ZD1839 polymorph.

We have also surprisingly found that the compound of Formula I can exist as a trihydrate (hereinafter Form 5 ZD1839 trihydrate) and that Form 5 ZD1839 trihydrate possesses advantageous properties.

Form 5 ZD1839 trihydrate is a stable form of the compound of Formula I In particular, Form 5 ZD1839 trihydrate is very stable in the presence of water. For example, when Form 5 ZD1839 trihydrate is prepared as an aqueous suspension the resulting suspension is stable, whereas aqueous suspensions prepared using other forms of the compound of Formula I are prone to convert to Form 5 ZD1839 trihydrate during storage. In the case of aqueous suspensions of the compound of Formula I this can be problematic because the conversion of a less thermodynamically stable form to the Form 5 ZD1839 trihydrate can result in the growth of large crystals of the Form 5 ZD1839 trihydrate, thereby altering the particle size distribution in the suspension. This may result in the suspension becoming unstable due to the sedimentation of the crystals which may grow as a result of the conversion from a less stable form to the more stable Form 5 ZD1839 trihydrate. Furthermore, if a variable mixture of two such forms of the compound of Formula I were to be present, the dissolution rate and bioavailability of the active compound(s) could be variable as a result of the different characteristics of the two forms.

Form 5 ZD1839 trihydrate may exhibit other physical properties such as crystalline size and shape, melting point, density and hygroscopicity that differ when compared to known forms of the compound of Formula I. Such differences may provide advantageous handling properties of the compound such as improved flow characteristics of the solid material and/or improved filtration during manufacture. Such advantages may provide improved formulation and processing of the compound of Formula I on a commercial scale. In particular the small needle or rod-like crystal habit of the Form 5 ZD1839 trihydrate provides a material with advantageous filtration properties and drying characteristics.

Moreover, Form 5 ZD1839 trihydrate may readily be prepared on a commercial scale at a high level of purity and in high yield. In addition Form 5 ZD1839 trihydrate can be readily converted into the Form 1 ZD1839 polymorph. The preparation of Form 5 ZD1839 trihydrate, purification thereof and conversion back to the Form 1 ZD1839 polymorph is beneficial in terms of yield and purity of the compound of the Form 1 ZD1839 polymorph, a form which is particularly suitable for use in solid formulations such as tablet and capsule formulations containing the compound of Formula I.

According to a further aspect of the invention there is provided 4-(3'-chloro-4'-fluoroanilino)-7-methoxy-6-(3-morpholinopropoxy)quinazoline trihydrate (Form 5 ZD1839 trihydrate).

According to a further aspect of the invention there is provided Form 5 ZD1839 trihydrate which is substantially free of any other ZD1839 solvate or ZD1839 polymorph such as for example Form 1 ZD1839 polymorph, Form 2 ZD1839 MeOH solvate or Form 3 ZD1839 DMSO.

The Form 5 ZD1839 trihydrate according to the present invention is highly crystalline. By "highly crystalline" is meant that the degree of crystallinity, as determined by X-ray powder diffraction data, is conveniently greater than about 60%, more conveniently greater than about 80%, particularly greater than about 90% and more particularly greater, than about 95%.

When it is stated that the present invention relates to Form 5 ZD1839 trihydrate, the molar ratio of ZD1839 to water is in the range 1:2.5 to 1:3.5, more particularly approximately 1:3.

When it is stated that the invention relates to Form 5 ZD1839 trihydrate substantially free of any other ZD1839 solvate or any other ZD1839 polymorph, this means that at least 80% of the compound of the Formula I is in the form of Form 5 ZD1839 trihydrate and less than 20% of the compound of the Formula I is in the form of any other ZD1839 solvate or any other ZD1839 polymorph. Particularly at least 90% and, in particular, at least 95% of the compound of the Formula I is in the form of Form 5 ZD1839 trihydrate.

Samples of the particular crystalline forms of the compound of the Formula I were analysed using a combination of X-Ray Powder Diffraction (hereinafter XRPD) analysis, Differential Scanning Calorimetry (hereinafter DSC), Thermal Gravimetric Analysis (hereinafter TGA), Diffuse Reflectance Infrared Fourier Transform (DRIFT) spectroscopy, Near Infrared (NIR) spectroscopy, solid state nuclear magnetic resonance spectroscopy and/or water content determination by Karl Fischer analysis.

X-ray diffraction data were obtained using Siemens D5000 equipment, the use of which is described in more detail hereinafter. It will be appreciated that different equipment and/or conditions may result in slightly different data being generated, for example there may be variation in the location and relative intensities of the peaks. In particular, the intensities of peaks measured using XRPD may vary as a result of particle size and shape because of the effects of the packing of the crystalline particles into XRPD mounts. Such packing effects are well known in the art and are often referred to as the "preferred orientation" effect. Preferred orientation in the specimen influences the intensities of various reflections so that some are more intense and others less, compared to that which would be expected from a completely random sample. Therefore, intensity variations can occur for the same sample, which are dependent on, for example, the particle size and shape. The preferred orientation effect is especially evident for needle-like or plate-like crystals when size reduction yields finer needles or platelets. As a result polymorphic forms are most reliably characterised primarily by peak positions in the X-ray diffractogram. These effects as well as methods for standard X-ray diffraction analysis can be found in, for example, Bunn, C. W. (1948), Chemical Crystallography, Clarendon Press, London; or Klug, H. P. & Alexander, L. E. (1974), X-Ray Diffraction Procedures, John Wiley and Sons, New York. Hence the figures quoted are not to be taken as absolute values.

The compound of Formula I in the form of Form 1 ZD1839 polymorph has the X-ray diffraction pattern shown in FIG. 1 hereinafter having characterising peaks [on the 2 theta (θ) scale] at about 7.0, 11.2, 15.8, 19.3, 24.0 (largest peak) and 26.3°.

Melting points and TGA were determined using Perkin Elmer Pyris 1 DSC/TGA equipment, the use of which is described in more detail hereinafter. It will be appreciated that alternative readings of melting point may be given by other types of equipment or by using conditions different to those described hereinafter. Hence the figures quoted are not to be taken as absolute values. The DSC thermogram and TGA for Form 1 ZD1839 polymorph is shown in FIG. 2 hereinafter. This polymorph has a melting point in the range of about 194° C. to 198° C. More particularly, the melting point is in the range of about 194.5° C. to 196.5° C. Most particularly, the melting point is in the range of about 195° C. to 196° C.

DRIFT spectroscopy data were obtained on a Nicolet 20SXC spectrometer, the use of which is described in more detail hereinafter. It will be appreciated that slightly different data may be generated if different equipment and/or conditions of sample preparation are used. Hence the figures quoted are not to be taken as absolute values. The DRIFT spectroscopy trace for Form 1 ZD1839 polymorph is shown in FIG. 3 hereinafter with distinguishing peaks at about 3400, 1630, 1525, 1245 and 840 cm$^{-1}$.

In addition, there is the potential for Form 1 ZD1839 polymorph to be characterised and/or distinguished from other physical forms by other techniques for example using NIR spectroscopy or solid state nuclear magnetic resonance spectroscopy.

In addition, the crystal structure of Form 1 ZD1839 polymorph was characterised by single-crystal X-ray analysis as described in more detail hereinafter. This polymorph crystallises in the triclinic space group P(−1) with two ZD1839 molecules in the unit-cell and the unit-cell dimensions are: a=8.876(1), b=9.692(1), c=12.543(1) Å, α=93.51(1), β=97.36, γ=101.70(1)° and v=1043.6(2) Å$^3$. Other data are shown in Tables A:1 and A:2 hereinafter within Example 5.

The compound of Formula I in the form of the metastable anhydrate ZD1839 polymorph when characterised by a DSC thermogram shows an initial exothermic event associated with conversion from the metastable form to Form 1 ZD1839 polymorph which, as disclosed hereinbefore, has an endothermic event corresponding to a melting point in the range of about 194° C. to 198° C.

The compound of Formula I in the form of Form 2 ZD1839 MeOH solvate has the X-ray powder diffraction pattern shown in FIG. 4 hereinafter having characterising peaks [on the 2 theta (θ) scale] at about 6.5 (largest peak), 10.0 and 13.2°.

The DSC thermogram and TGA for Form 2 ZD1839 MeOH solvate is shown in FIG. 5 hereinafter. The trace shows an initial endotherm at approximately 130° C. and a second endotherm at approximately 196° C. The second endotherm corresponds to that from the DSC thermogram from Form 1 ZD1839 polymorph and indicates that desolvation and a conversion to Form 1 ZD1839 polymorph has occurred on heating. The TGA shows a solvent loss of approximately 3% by weight at approximately 130° C. Thus Form 2 ZD1839 MeOH solvate has a desolvation point in the range of about 110° C. to 140° C. More particularly, the desolvation point is in the range of about 125° C. to 138° C.; even more particularly, in the range of about 125° C. to 130° C.

The DRIFT spectroscopy trace for Form 2 ZD1839 MeOH solvate is shown in FIG. 6 hereinafter with distinguishing peaks at about 3380, 1650, 1530, 1450, 1235, 870 and 570 cm$^{-1}$.

The compound of Formula I in the form of Form 3 ZD1839 DMSO solvate has the X-ray powder diffraction pattern shown in FIG. 7 hereinafter having characterising peaks [on the 2 theta (θ) scale] at about 8.9, 17.8, 22.6 (largest peak) and 23.2°.

The DSC thermogram and TGA for Form 3 ZD1839 DMSO solvate is shown in FIG. 8 hereinafter. The TGA shows a solvent loss of approximately 14% by weight over a temperature range of approximately 80 to 105° C. The DSC trace shows an endotherm at approximately 130° C. Thus Form 3 ZD1839 DMSO solvate has a desolvation point in the range of about 125° C. to 135° C. More particularly, the desolvation point is in the range of about 127° C. to 132° C. Most particularly, the desolvation point is about 130° C.

The DRIFT spectroscopy trace for Form 3 ZD1839 DMSO solvate is shown in FIG. 9 hereinafter with distinguishing peaks at about 1640, 1520, 1450, 880 and 560 cm$^{-1}$.

The Form 5 ZD1839 trihydrate according to the present invention has the X-ray diffraction pattern shown in FIG. 10 hereinafter having characterising peaks [on the 2 theta (θ) scale] at about the positions shown in Table 1 below:

TABLE 1

| 2 theta | Relative intensity |
|---------|--------------------|
| 6.1     | S                  |
| 7.1     | VS                 |
| 9.3     | VS                 |
| 14.2    | VS                 |
| 18.5    | VS                 |
| 18.8    | VS                 |
| 19.8    | VS                 |
| 22.3    | VS                 |
| 23.3    | VS                 |
| 24.7    | VS                 |
| 25.7    | VS                 |

In particular, the first peak (at 6.1° on the 2θ scale) in Table 1 is unique to Form 5 ZD1839 trihydrate and is not present in any other known form of the compound of Formula I. Further large characterising peaks are also observed at 7.1° and 25.7° on the 2θ scale.

As mentioned hereinbefore, the intensities of the peaks in the XRPD diffractogram may exhibit some variability, depending upon the measurement conditions used. Accordingly, in Table 1 and as quoted hereinafter, relative intensities are not stated numerically. Instead the following definitions for intensity are used:

| % Relative Intensity* | Definition      |
|-----------------------|-----------------|
| 25-100                | VS (very strong)|
| 10-25                 | S (strong)      |
| 3-10                  | M (medium)      |
| 1-3                   | W (weak)        |

*The relative intensities are derived from X-ray diffraction patterns measured with variable slits.

As will be clear some of the more minor peaks present in the X-ray diffraction pattern in FIG. 10 have been omitted from Table 1.

Melting point and weight loss during heating on the Form 5 ZD1839 trihydrate were determined using DSC and TGA respectively using Mettler DSC820E and TG851 with TSO891RO robotic systems, the use of which is described in more detail hereinafter in the Examples. It will be appreciated that alternative readings of melting point may be given by other types of equipment or by using conditions different to those described hereinafter. Hence the figures quoted are not to be taken as absolute values. The DSC thermogram and TGA for Form 5 ZD1839 trihydrate is shown in FIG. 11 hereinafter.

The DSC trace in FIG. 11 shows a first endotherm with a peak value at approximately 100° C. (onset at approximately 89° C.) and a second endotherm is observed with a peak at about 194° C. to 198° C., particularly at about 196° C. The second endotherm is a melting endotherm (onset temperature approximately 195° C.). The second endotherm corresponds with the melting point of Form 1 ZD1839 polymorph and suggests dehydration and a conversion to Form 1 ZD1839 polymorph has occurred on heating the Form 5 ZD1839 trihydrate. The TGA thermogram in FIG. 11 shows an event equivalent to that seen in the DSC trace reflecting loss of water of hydration of about 10.8%, which corresponds to the water content of the trihydrate of the compound of Formula I (theoretical water content loss for trihydrate is 10.79%). No other events were observable on the DSC trace. Thus Form 5 ZD1839 trihydrate has a dehydration point in the range of about 70° C. to 120° C. More particularly, the dehydration point is in the range of about 80 to 105° C.; even more particularly, in the range of about 88 to 100° C.

In addition, the crystal structure of Form 5 ZD1839 trihydrate may be characterised by its unit cell dimensions, determined by single-crystal X-ray analysis as described in more detail hereinafter. Form 5 ZD1839 trihydrate according to the present invention is further characterized by a monoclinic unit cell with parameters: a=14.41 Å, b=24.89 Å, c=6.81 Å, $\alpha$=90°, $\beta$=92.2°, $\gamma$=90° and v=2440.4 Å$^3$. The unit cell data was determined as described in the Examples. Other single crystal data are shown in the Tables B1 and B2 within Example 9.

The following particular crystalline forms of the compound of the Formula I are disclosed herein:—
 (i) Form 3 ZD1839 DMSO solvate;
 (ii) Form 2 ZD1839 MeOH solvate;
 (iii) Form 1 ZD1839 polymorph; and
 (iv) Form 5 ZD1839 trihydrate.

Each of these entities possesses the same pharmacological properties as those disclosed in International Patent Application WO 96/33980 for compounds such as 4-(3'-chloro-4'-fluoroanilino)-7-methoxy-6-(3-morpholnopropoxy) quinazoline, in particular anti-proliferative activity such as anti-cancer activity. These solvate, hydrate and polymorph entities are described collectively hereinafter as 'the active substance of the invention'.

In order to use the active substance of the invention for the treatment of mammals including humans, it is normally formulated in accordance with standard pharmaceutical practice as a pharmaceutical composition. Therefore, according to another aspect of the invention there is provided a pharmaceutical composition which comprises the active substance of the invention and a pharmaceutically-acceptable diluent or carrier.

For example, the compositions of the invention may be in a form adapted for oral administration (for example as tablets, lozenges, hard or soft capsules, aqueous or oily suspensions, emulsions, dispersible powders or granules, syrups or elixirs), for topical administration (for example as creams, ointments, gels, or aqueous or oily solutions or suspensions), for insufflation (for example as an aqueous suspension) or for parenteral administration (for example as a sterile aqueous or oily solution for intravenous, subcutaneous, intraperitoneal or intramuscular dosing or as a suppository for rectal dosing).

A preferred method of administration is oral administration. The active substance of the invention is conveniently administered orally in the form of tablets. Specific examples of tablet formulations are described hereinafter.

The compositions of the invention may be obtained by conventional procedures using conventional pharmaceutical excipients that are well known in the art. Thus, compositions intended for oral use may contain, for example, one or more colouring, sweetening, flavouring and/or preservative agents.

Standard excipients include, for example, tablet diluents, dispersants, suspending and binding agents, structure formers, tablet lubricants, cryoprotectants and pH modifiers, such as mannitol, sorbitol, lactose, glucose, sodium chloride, acacia, dextran, sucrose, maltose, gelatin, bovine serum albumin (BSA), glycine, mannose, ribose, polyvinylpyrrolidinone (PVP), cellulose derivatives such as microcrystalline cellulose, glutamine, inositol, potassium glutamate, magnesium stearate, sodium lauryl sulphate, talc, erythritol, serine and other amino acids, calcium carbonate, magnesium carbonate and other weak bases, and buffer agents, for example disodium hydrogen phosphate, calcium hydrogen phosphate and potassium citrate.

As mentioned herein, the Form 5 ZD1839 trihydrate is particularly stable in the presence of water. Accordingly Form 5 ZD1839 trihydrate is particularly suitable for administration as an aqueous suspension formulation. Conventional aqueous suspension formulations are well known in the art. A suitable suspension formulation comprises, for example, a suspension of Form 5 ZD1839 trihydrate in water, a nonionic surfactant, a water-soluble soluble salt and optionally a pH buffer. Suitable non-ionic surfactants include, for example, Polysorbates such as Polysorbate 20. The water-soluble salt may be sodium chloride, in an amount sufficient to render the suspension isotonic. When a buffer is present, it will suitably be chosen to maintain the pH of the suspension at about 7, for example a pH 7 phosphate buffer.

The amount of the active substance of the invention that is combined with one or more excipients to produce a single dosage form will necessarily vary depending upon the host treatment and the particular route of administration. For example, a formulation intended for oral administration to humans will conveniently contain, for example, from 1 mg to 1 g of active substance compounded with an appropriate and convenient amount of excipient which may vary from about 5 to about 98 percent by weight of the total composition. Preferably the formulation will comprise, for example, from 50 mg to 750 mg of active substance. More preferably the formulation will comprise, for example, from 100 mg to 500 mg of active substance, especially about 250 mg of active substance.

In using the active substance of the invention for therapeutic or prophylactic purposes it will generally be administered so that a daily dose in the range, for example, 0.2 to 20 mg per kg body weight is received, given if required in divided doses. Preferably a daily dose in the range, for example, 0.5 to 15 mg per kg body weight is received. More preferably a daily dose in the range, for example, 1 to 10 mg per kg body weight is received.

The active substance of the invention shows an acceptable toxicity profile.

Further details of the uses of the compound of the Formula I and combinations containing the compound are disclosed in International Patent Application WO 96/33980. The active substance of the invention possesses the same pharmacological properties as those disclosed in International Patent Application WO 96/33980 for the compound of the Formula I, in particular anti-proliferative activity such as anti-cancer activity. For example, the active substance of the invention is useful for the treatment of many common human cancers such as lung (including small cell lung cancer and non small cell lung cancer), breast, prostate, ovarian, colorectal, gastric, brain (including glioma and pituitary adenoma), head and neck, bladder, pancreas, oesophageal, stomach, renal, skin (including malignant melanoma), gynaecological (including cervical, endometrial, vaginal, vulval and uterine) and thyroid cancer and in the treatment of a range of leukaemias, lymphoid malignancies and solid tumours such as carcinomas and sarcomas. It is further expected that the active substance of the invention will be useful for the treatment of other diseases involving excessive cellular proliferation such as benign skin hyperplasia, for example psoriasis, and benign prostatic hypertrophy (BPH).

The pharmacological properties of the active substance of the invention may be assessed using, for example, one or more of the test procedures disclosed in International Patent Application WO 96/33980 or equivalent test procedures that are well within the compass of the man skilled in the art. Such test procedures from that patent application are incorporated herein by reference.

According to a further aspect of the present invention there is provided the active substance of the invention as defined hereinbefore for use in a method of treatment of the human or animal body by therapy.

We have found that the active substance of the invention possesses anti-proliferative properties such as anti-cancer properties which are believed to arise from its EGF receptor (erbB1) tyrosine kinase inhibitory activity. Accordingly the active substance of the invention is expected to be useful in the treatment of diseases or medical conditions mediated alone or in part by erbB1 receptor tyrosine kinases, i.e. the active substance of the invention may be used to produce an erbB1 receptor tyrosine kinase inhibitory effect in a warm-blooded animal in need of such treatment. Thus the active substance of the invention provides a method for treating the proliferation of malignant cells characterised by inhibition of erbB1 receptor tyrosine kinases, i.e. the active substance of the invention may be used to produce an anti-proliferative effect mediated alone or in part by the inhibition of erbB1 receptor tyrosine kinase. Accordingly the active substance of the invention is expected to be useful in the treatment of psoriasis and/or cancer by providing an anti-proliferative effect, particularly in the treatment of erbB1 receptor tyrosine kinase sensitive cancers such as lung, breast, prostate, ovarian, colorectal, gastric, brain, head and neck, bladder, pancreas, oesophageal, stomach, renal, skin, gynaecological and thyroid cancer.

Thus according to this aspect of the invention there is provided the active substance of the invention as defined hereinbefore for use in the production of an anti-proliferative effect in a warm-blooded animal such as man.

Further, according to this aspect of the invention there is provided the use of the active substance of the invention as defined hereinbefore in the manufacture of a medicament for use in the production of an anti-proliferative effect in a warm-blooded animal such as man.

According to a further feature of this aspect of the invention there is provided a method for producing an anti-proliferative effect in a warm-blooded animal, such as man, in need of such treatment which comprises administering to said animal an effective amount of the active substance of the invention as defined hereinbefore.

As stated above the size of the dose required for the therapeutic or prophylactic treatment of a particular proliferative disease will necessarily be varied depending on the host treated, the route of administration and the severity of the illness being treated. Preferably a daily dose in the range, for example, 0.5 to 15 mg per kg body weight is received. More preferably a daily dose in the range, for example, 1 to 10 mg per kg body weight is received. A unit dose in the range, for example, 1 to 1000 mg, conveniently 100 to 750 mg, more conveniently 200 to 600 mg, preferably about 250 mg is envisaged.

The active substance of the invention defined hereinbefore may be applied as a sole therapy or may involve, in addition to the active substance of the invention, conventional surgery and/or radiotherapy and/or chemotherapy. Such chemotherapy may include one or more of the following categories of anti-cancer agents:—

(i) anti-invasion agents [for example metalloproteinase inhibitors such as MMP-2 (matrix-metalloproteinase-2) and MMP-9 (matrix-metalloproteinase-9) inhibitors, for example marimastat, and inhibitors of urokinase plasminogen activator receptor function];

(ii) antiproliferative/antineoplastic drugs and combinations thereof, as used in medical oncology, such as alkylating agents (for example cis-platin, carboplatin, cyclophosphamide, nitrogen mustard, melphalan, chlorambucil, busulphan and nitrosoureas); antimetabolites (for example antifolates such as fluoropyrimidines like 5-fluorouracil and tegafur, raltitrexed, methotrexate, cytosine arabinoside and hydroxyurea, or, for example, one of the preferred antimetabolites disclosed in European Patent Application No. 562734 such as (2S)-2-{o-fluoro-p-[N-{2,7-dimethyl-4-oxo-3,4-dihydroquinazolin-6-ylmethyl)-N-(prop-2-ynyl) amino]benzamido}-4-(tetrazol-5-yl)butyric acid); antitumour antibiotics (for example anthracyclines like adriamycin, bleomycin, doxorubicin, daunomycin, epirubicin, idarubicin, mitomycin-C, dactinomycin and mithramycin); antimitotic agents (for example vinca alkaloids like vincristine, vinblastine, vindesine and vinorelbine and taxoids like taxol and taxotere); and topoisomerase inhibitors (for example epipodophyllotoxins like etoposide and teniposide, amsacrine, topotecan and camptothecin);

(iii) cytostatic agents such as antioestrogens (for example tamoxifen, fulvestrant, toremifene, raloxifene, droloxifene and iodoxyfene), antiandrogens (for example bicalutamide, flutamide, nilutamide and cyproterone acetate), LHRH antagonists or LHRH agonists (for example goserelin, leuprorelin and buserelin), progestogens (for example megestrol acetate), aromatase inhibitors (for example as anastrozole, letrazole, vorazole and exemestane) and inhibitors of 5α-reductase such as finasteride;

(iv) other inhibitors of growth factor function, for example growth factor antibodies, growth factor receptor antibodies such as C225, antibodies to components of the signal transduction cascade, for example antibodies to erbB2 such as trastuzumab, tyrosine kinase inhibitors and serine/threonine kinase inhibitors, for example other inhibitors of the epidermal growth factor family such as N-(3-ethynylphenyl)-6,7-bis(2-methoxyethoxy)quinazolin-4-amine (OSI-774) and 6-acrylamido-N-(3-chloro-4-fluorophenyl)-7-(3-morpholinopropoxy)quinazolin-4-amine (CI 1033), for example inhibitors of the platelet-derived growth factor family, for example inhibitors of the protein product of the bcr-abl gene such as imatinib (STI571), for example inhibitors of the fibroblast growth factor family and for example inhibitors of the hepatocyte growth factor family;

(v) antiangiogenic agents such as those which inhibit vascular endothelial growth factor such as the compounds disclosed in International Patent Applications WO 97/22596, WO 97/30035, WO 97/32856, WO 98/13354, WO 00/47212 and WO 01/32651 and those that work by other mechanisms (for example linomide, inhibitors of integrin αvβ3 function and angiostatin);

(vi) cyclooxygenase-2 (COX-2) inhibitors such as celecoxib and rofecoxib;

(vii) vascular damaging agents such as Combretastatin A4 and compounds disclosed in International Patent Applications WO 99/02166, WO 00/40529, WO 00/41669, WO 01/92224, WO 02/04434 and WO 02/08213;

(viii) antisense therapies, for example those which are directed to the targets listed above, such as ISIS 2503, an anti-ras antisense;

(ix) gene therapy approaches, including for example approaches to replace aberrant genes such as aberrant p53 or aberrant BRCA1 or BRCA2, GDEPT (gene-directed enzyme pro-drug therapy) approaches such as those using cytosine deaminase, thymidine kinase or a bacterial nitroreductase enzyme and approaches to increase patient tolerance to chemotherapy or radiotherapy such as multi-drug resistance gene therapy; and (x) immunotherapy approaches, including for example ex-vivo and in-vivo approaches to increase the immunogenicity of patient tumour cells, such as transfection with cytokines such as interleukin 2, interleukin 4 or granulocyte-macrophage colony stimulating factor, approaches to decrease T-cell anergy, approaches using transfected immune cells such as cytokine-transfected dendritic cells, approaches using cytokine-transfected tumour cell lines and approaches using anti-idiotypic antibodies.

Such conjoint treatment may be achieved by way of the simultaneous, sequential or separate dosing of the individual components of the treatment. Such combination products employ the compounds of this invention within the dosage range described hereinbefore and the other pharmaceutically-active agents within their approved dosage ranges.

According to this aspect of the invention there is provided a pharmaceutical product comprising the active substance of the invention as defined hereinbefore and an additional anti-cancer agent as defined hereinbefore for the conjoint treatment of cancer.

Processes for the preparation of the following particular crystalline forms of the compound of the Formula I are disclosed herein, namely processes:—
(i) for preparing Form 3 ZD1839 DMSO solvate;
(ii) for preparing Form 2 ZD1839 MeOH solvate;
(iii) for preparing Form 1 ZD1839 polymorph; and
(iv) for preparing Form 5 ZD1839 trihydrate.

We have discovered a process for preparing a crystalline form of the compound of the Formula I substantially in the form of Form 3 ZD1839 DMSO solvate, preferably substantially free of any other ZD1839 solvate or any Form 1 ZD1839 polymorph. Such a process provides a further aspect of the present invention and comprises, for example, the steps of:—

(a) heating a mixture of the compound 4-(3'-chloro-4'-fluoroanilino)-7-methoxy-6-(3-morpholinopropoxy)quinazoline in dimethyl sulphoxide or a solvent mixture containing dimethyl sulphoxide and a co-solvent until dissolution has occurred;

(b) reducing the temperature of the solvent system to induce nucleation;

(c) maintaining the mixture at a temperature below that at which nucleation has commenced; and (d) isolating the crystalline solid so deposited.

The mixture may, for example, be heated to reflux until dissolution has occurred. Alternatively, the mixture may, for example, be heated to a temperature less than the reflux temperature of the solvent provided that dissolution of more or less all of the solid material has occurred. It will be appreciated that small quantities of insoluble material may be removed by filtration of the warmed mixture.

Suitable solvent mixtures include dimethyl sulphoxide and one or more co-solvents such as a polar protic solvent such as ethanol and isopropanol and/or a non-protic solvent such as tetrahydrofuran, acetone, ethyl acetate and N,N-dimethylformamide. For example, a suitable solvent is dimethyl sulphoxide. A further suitable solvent is a mixture of dimethylsulphoxide and ethyl acetate wherein the ratio by volume of ethyl acetate to dimethyl sulphoxide lies within the range 50:1 to 0.05:1, conveniently in the range 20:1 to 0.5:1, for example 1 part of ethyl acetate and 1 part of dimethyl sulphoxide, 6 parts of ethyl acetate and 1 part of dimethyl sulphoxide or 13 parts of ethyl acetate and 1 part of dimethyl sulphoxide.

The solution of the compound 4-(3'-chloro-4'-fluoroanilino)-7-methoxy-6-(3-morpholinopropoxy)quinazoline in dimethyl sulphoxide or a solvent mixture containing dimethyl sulphoxide as one component may be removed from the heat source and allowed to cool to ambient temperature or it may be cooled further, for example to about 0° C. in a bath of ice and water. Alternatively, the solution may be cooled at a controlled rate to about 0° C. A suitable cooling rate is, for example, about 10° C. per hour.

It will be appreciated that nucleation may occur either spontaneously or on adding one or more seed crystals.

It has been noted that, on occasions, some Form 1 ZD1839 polymorph may crystallise from the solution of 4-(3'-chloro-4'-fluoroanilino)-7-methoxy-6-(3-morpholinopropoxy) quinazoline and that such material is transformed into Form 3 ZD1839 DMSO solvate in the presence of the DMSO in the solvent mixture. The rate of said transformation is temperature dependent, transformation having been noted at ambient temperature and more rapid transformation having been noted at higher temperatures, for example in the range of about 30 to 50° C., conveniently at about 40° C. However, it has also been noted that at temperatures of above about 50° C. Form 3 ZD1839 DMSO solvate is transformed back to Form 1 ZD1839 polymorph. Accordingly, in an improved version of the above-mentioned process for preparing a crystalline form of the compound of the Formula I substantially in the form of Form 3 ZD1839 DMSO solvate, once the mixture has been maintained at a temperature below that at which nucleation has commenced, a step is added of reheating the mixture to a temperature in the range of about 30° C. to 50° C., conveniently to about 40° C., for example for a period of about 1 hour, followed by reducing the temperature of the mixture to about 0° C. to complete the crystallisation.

The crystalline solid may be isolated by any conventional method, for example by filtration or centrifugation.

It will be appreciated by the man skilled in the art that the procedures described above may be varied using routine skill and knowledge. For example, provided that a crystalline form of the compound of the Formula I substantially in the form of Form 3 ZD11839 DMSO solvate is obtained, any of the quantity of the compound 4-(3'-chloro-4'-fluoroanilino)-7-methoxy-6-(3-morpholinopropoxy)quinazoline that is treated, the volume of the DMSO solvent, the nature and volume of any co-solvent, the ratio of the component solvents if a solvent mixture is employed and the temperatures of the dissolution and cooling phases may be varied.

It will also be appreciated that, when nucleation is induced during any of the process procedures described herein by the addition of one or more seed crystals, a quantity of seed crystals having a weight in the range of about 1 to 500 mg may be employed. Preferably a quantity of seed crystals having a weight in the range of about 1 to 100 mg may be employed.

In addition Form 3 ZD1839 DMSO solvate may readily be converted into the compound of Formula I, particularly into Form 1 ZD1839 polymorph. Overall, the inclusion of the steps of DMSO solvate preparation, purification thereof and conversion into Form 1 ZD1839 polymorph is beneficial in terms of the yield and purity of the Form 1 ZD1839 polymorph so obtained. Such a process for the preparation of the compound of Formula I substantially in the form of Form 1 ZD1839 polymorph provides a further aspect of the present invention and comprises, for example, the steps of:—

(a) washing Form 3 ZD1839 DMSO solvate with a solvent or solvent mixture substantially to remove dimethyl sulphoxide; and (b) isolating the Form 1 ZD1839 polymorph so formed.

Suitable solvents include, for example, a polar protic solvent such as ethanol or isopropanol or a non-protic solvent such as tetrahydrofuran, acetone, ethyl acetate or N,N-dimethylformamide. Mixtures of such solvents may also be employed. Ethyl acetate is a preferred solvent for this washing procedure. Conveniently the washing solvent may be warmed, for example to a temperature of about 30° C. to 50° C.

It is to be understood that the 'washing' step requires a suitable period of time. For example, if the Form 3 ZD1839 DMSO solvate is held on a filter apparatus and the washing solvent is passed through that solid too quickly the conversion to Form 1 ZD1839 polymorph will be incomplete. A suitable contact time between the solid and washing solvent is in the range of about 5 minutes to 1 or more hours. More conveniently, the contact time is in the range of about 30 minutes to about 2 hours, for example about 1 hour. Conveniently, a slurry of the solid and the washing solvent is prepared. Conveniently, the slurry is stirred to improve contact between the washing solvent and the crystals of solid. As stated above, conveniently the washing solvent may be warmed. It will be appreciated that, during the washing step, portions of the Form 3 ZD1839 DMSO solvate are dissolved in the washing solvent and from the solution so formed Form 1 ZD1839 polymorph crystallises. However, it is not necessary for all of the Form 3 ZD1839 DMSO solvate to be in solution prior to the commencement of the crystallisation of the Form 1 ZD1839 polymorph. Hence the washing step described herein concerns a portionwise dissolution and conversion of form of the Form 3 ZD1839 DMSO solvate.

The crystalline solid may be isolated by any conventional method, for example by filtration or centrifugation.

Conveniently, the compound of Formula I substantially in the form of Form 1 ZD1839 polymorph that is obtained from the washing step may be purified further by recrystallisation. For example, the washed solid may be warmed in a suitable solvent as defined hereinbefore until dissolution has occurred, the temperature of the solution may be reduced to induce nucleation either spontaneously or on adding one or more seed crystals, the temperature of the solution may be maintained below that at which nucleation has commenced and the crystalline solid so deposited may be isolated.

We have also discovered a process for preparing a crystalline form of the compound of the Formula I substantially in the form of Form 2 ZD1839 MeOH solvate, preferably substantially free of any other ZD1839 solvate or any Form 1 ZD1839 polymorph. Such a process provides a further aspect of the present invention and comprises, for example, the steps of:—

(a) heating a mixture of the compound 4-(3'-chloro-4'-fluoroanilino)-7-methoxy-6-(3-morpholinopropoxy) quinazoline in methanol or a solvent mixture containing methanol and a co-solvent until dissolution has occurred;

(b) reducing the temperature of the solvent system to induce nucleation;

(c) maintaining the mixture at a temperature below that at which nucleation has commenced; and (d) isolating the crystalline solid so deposited.

The mixture may, for example, be heated to reflux until dissolution has occurred. The mixture may then be removed from the heat source and allowed to cool to ambient temperature or it may be cooled further, for example to about 0° C. in a bath of ice and water. Alternatively, the solution may be cooled at a controlled rate to about 0° C. A suitable cooling rate is, for example, about 10° C. per hour.

It will be appreciated that nucleation may occur either spontaneously or on adding one or more seed crystals.

Suitable solvent mixtures include methanol and one or more co-solvents such as weakly polar solvents, for example aromatic hydrocarbons such as toluene, halogeno-(1-6C)alkanes such as 1,2-dichloroethane and aliphatic di-(1-6C) alkyl ethers or (4-7C)cyclic ethers such as tetrahydrofuran, other polar protic solvent such as ethanol and isopropanol, polar non-protic solvents such as aliphatic esters such as ethyl acetate, aliphatic (3-6C)ketones such as acetone and aliphatic amides such as N,N-dimethylformamide. For example, a suitable solvent is methanol. A further suitable solvent is a mixture of methanol and a co-solvent selected from toluene and ethyl acetate where, for example, the ratio by volume of co-solvent to methanol lies within the range 50:1 to 0.05:1, conveniently in the range 20:1 to 0.5:1.

The solution of the compound 4-(3'-chloro-4'-fluoroanilino)-7-methoxy-6-(3-morpholinopropoxy)quinazoline in methanol or a solvent mixture containing methanol as one component may be removed from the heat source and cooled as described hereinbefore for the preparation of Form 3 ZD1839 DMSO solvate.

The crystalline solid may be isolated by any conventional method, for example by filtration or centrifugation.

It will be appreciated by the man skilled in the art that the procedures described above may be varied using routine skill and knowledge. For example, provided that a crystalline form of the compound of the Formula I substantially in the form of Form 2 ZD1839 MeOH solvate is obtained, any of the quantity of the compound 4-(3'-chloro-4'-fluoroanilino)-7-methoxy-6-(3-morpholinopropoxy)quinazoline that is treated, the volume of the methanol solvent, the nature and volume of any co-solvent, the ratio of the component solvents if a solvent mixture is employed and the temperatures of the dissolution and cooling phases may be varied.

In addition Form 2 ZD1839 MeOH solvate may be converted into the compound of Formula I, particularly into Form 1 ZD1839 polymorph. Such a process for the preparation of the compound of Formula I in the form of Form 1 ZD1839 polymorph provides a further aspect of the present invention and comprises, for example, the steps of:—

(a) washing Form 2 ZD1839 MeOH solvate with a solvent or solvent mixture substantially to remove methanol; and (b) isolating the Form 1 ZD1839 polymorph so formed.

Suitable solvents include, for example, a polar protic solvent such as ethanol or isopropanol or a non-protic solvent such as tetrahydrofuran, acetone, ethyl acetate or N,N-dimethylformamide. Mixtures of such solvents may also be employed. Ethyl acetate is a preferred solvent for this washing procedure. Conveniently the washing solvent may be warmed, for example to a temperature of about 30° C. to 50° C.

It will be appreciated that the washing step as described herein concerns a portionwise dissolution and conversion of form of the Form 2 ZD1839 MeOH solvate.

The crystalline solid may be isolated by any conventional method, for example by filtration or centrifugation.

Conveniently, the compound of Formula I substantially in the form of Form 1 ZD1839 polymorph that is obtained from the washing step may be purified further by recrystallisation. For example, the washed solid may be warmed in a suitable solvent as defined hereinbefore until dissolution has occurred, the temperature of the solution may be reduced to induce nucleation either spontaneously or on adding one or more seed crystals, the temperature of the solution may be maintained below that at which nucleation has commenced and the crystalline solid so deposited may be isolated.

In addition, Form 2 ZD1839 MeOH solvate may be converted into the compound of Formula I in the form of Form 1 ZD1839 polymorph by warming the compound, for example by heating the compound to a temperature of about 125° C. to 150° C., more particularly to a temperature of more than about 135° C.

A process for preparing a crystalline form of the compound of the Formula I substantially in the form of Form 1 ZD1839 polymorph has also been obtained. Preferably, the crystalline form of the compound of the Formula I substantially in the form of Form 1 ZD1839 polymorph is obtained substantially free of any other polymorphic form of ZD1839 or of any ZD1839 solvate. Such a process comprises, for example, the steps of:—

(a) dissolving the compound 4-(3'-chloro-4'-fluoroanilino)-7-methoxy-6-(3-morpholinopropoxy)quinazoline in a solvent system in which solvate formation is repressed;

(b) reducing the temperature of the solvent system to induce nucleation;

(c) maintaining the mixture at a temperature below that at which nucleation has commenced; and (d) isolating the crystalline solid so deposited.

Suitable solvent systems in which solvate formation is repressed include weakly polar solvents, for example aromatic hydrocarbons such as toluene, halogeno-(1-6C)alkanes such as 1,2-dichloroethane and aliphatic di-(1-6C)alkyl ethers or (4-7C) cyclic ethers such as tetrahydrofuran, more polar protic solvents, for example (2-6C) alcohols such as ethanol and isopropanol, and polar non-protic solvents such as aliphatic esters such as ethyl acetate, aliphatic (3-6C) ketones such as acetone and aliphatic amides such as N,N-dimethylformamide. Mixtures of such solvents may also be employed such as a mixture of toluene and isopropanol where, for example, the ratio by volume of toluene to isopropanol conveniently lies within the range 5:1 to 0.2:1, more conveniently in the range 2:1 to 0.5:1.

The solution of the compound 4-(3'-chloro-4'-fluoroanilino)-7-methoxy-6-(3-morpholinopropoxy)quinazoline may be removed from the heat source and allowed to cool to ambient temperature or it may be cooled further, for example to about 0° C. in a bath of ice and water. Alternatively, the solution may be cooled at a controlled rate to about 0° C. A suitable cooling rate is, for example, about 10° C. per hour. It will be appreciated that the nucleation may occur either spontaneously or on adding one or more seed crystals. The crystalline solid so obtained may be isolated by any conventional method, for example by filtration or centrifugation.

Conveniently, the solution of the compound 4-(3'-chloro-4'-fluoroanilino)-7-methoxy-6-(3-morpholinopropoxy) quinazoline may be removed from the heat source and allowed to cool to about 30° C. The mixture may be reheated to about 50° C. The mixture may then be allowed to cool to ambient temperature or it may be cooled further, for example to about 0° C. in a bath of ice and water. Alternatively, the solution may be cooled from about 50° C. at a controlled rate to about 0° C. A suitable cooling rate is, for example, about 10° C. per hour. The crystalline solid so obtained may be isolated by any conventional method, for example by filtration or centrifugation.

It will be appreciated by the man skilled in the art that the procedures described above may be varied using routine skill and knowledge. For example, provided that Form 1 ZD1839 polymorph is obtained substantially free of any other ZD1839 polymorph or any ZD1839 solvate, any of the quantity of the compound 4-(3'-chloro-4'-fluoroanilino)-7-methoxy-6-(3-morpholinopropoxy)quinazoline that is treated, the nature and volume of the solvent and any co-solvent, the ratio of the component solvents if a solvent mixture is employed and the temperatures of the dissolution and cooling phases may be varied. For example, a solution of the compound of the Formula I in a suitable solvent, for example a (2-6C) alcohol such as ethanol may be allowed to become concentrated by the evaporation of some of the solvent. Thereby a supersaturated solution is obtained from which Form 1 ZD1839 polymorph crystallises.

In a further aspect of the present invention there is provided a process for preparing a compound of the Formula I substantially in the form of Form 5 ZD1839 trihydrate (preferably substantially free of any other ZD1839 solvate or any other form of ZD1839) which comprises:—

(a) contacting 4-(3'-chloro-4'-fluoroanilino)-7-methoxy-6-(3-morpholinopropoxy)quinazoline with water for a sufficient time to convert the (3'-chloro-4'-fluoroanilino)-7-methoxy-6-(3-morpholinopropoxy)quinazoline to the Form 5 trihydrate; and (b) isolating the Form 5 ZD1839 trihydrate.

The 4-(3'-chloro-4'-fluoroanilino)-7-methoxy-6-(3-morpholinopropoxy)quinazoline used as the starting material in step (a) of the process may be any form of the compound of Formula I, for example prepared as described in the prior art or prepared as one of the forms described herein, particularly Form 1 ZD1839 polymorph.

Conveniently, conversion to the Form 5 ZD1839 trihydrate is effected by preparing a slurry of the 4-(3'-chloro-4'-fluoroanilino)-7-methoxy-6-(3-morpholinopropoxy)quinazoline starting material in water, optionally in the presence of one or more suitable organic solvent(s). Generally a molar excess of water is used to ensure substantially complete conversion of the 4-(3'-chloro-4'-fluoroanilino)7-methoxy-6-(3-morpholinopropoxy)quinazoline starting material to the Form 5 ZD1839 trihydrate (i.e. the molar ratio of water: 4-(3'-chloro-4'-fluoroanilino)7-methoxy-6-(3-morpholinopropoxy) quinazoline is at least 3:1). The upper limit of water concentration is not critical, however, generally a large molar excess of water is used. For example the molar ratio of water to 4-(3'-chloro-4'-fluoroanilino)-7-methoxy-6-(3-morpholinopropoxy)quinazoline is suitably from about 3:1 to 1000:1 or more, particularly from about 3:1 to about 400:1.

In a particular embodiment, a slurry of the 4-(3'-chloro-4'-fluoroanilino)-7-methoxy-6-(3-morpholinopropoxy) quinazoline starting material (such as Form 1 ZD1839 polymorph) is prepared in a mixture of water and an organic solvent, and optionally one or more co-solvents. We have found that the use of an organic solvent significantly reduces the time required to convert the starting material to the Form 5 ZD1839 trihydrate. Suitable organic solvents are water-miscible polar organic solvents, such as polar protic solvents, for example (1-4C) alcohols, particularly ethanol and isopropanol, polar non-protic solvents such as aliphatic esters, for example a (1-4C) allyl (2-3C)alkanoate ester, particularly ethyl acetate, aliphatic (3-6C) ketones such as acetone or aliphatic amides such as N,N-dimethylformamide. Particular solvents include, for example isopropanol or ethyl acetate, or a mixture thereof.

The amount of organic solvent used is generally insufficient to completely dissolve the 4-(3'-chloro-4'-fluoroanilino)-7-methoxy-6-(3-morpholinopropoxy)quinazoline starting material such that a slurry is retained throughout the process. We have found that by retaining the compound of the Formula I in a slurry during the process enables the ZD1839 trihydrate to be formed without the need to induce crystallisation by, for example, cooling the mixture or evaporating solvent. Accordingly the slurry process may be operated at a substantially constant temperature.

Without wishing to be bound by theory, it is thought that the conversion process proceeds via a mechanism of localised dissolution of the 4-(3'-chloro-4'-fluoroanilino)-7-methoxy-6-(3-morpholinopropoxy)quinazoline starting material and subsequent recrystallisation to the Form 5 ZD1839 trihydrate. Hence the slurry conversion process described herein is thought to be a portionwise dissolution and conversion of the starting material to the Form 5 ZD1839 trihydrate.

The specific amount of organic solvent used will be dependent upon the organic solvent selected and the conditions under which the slurry is contacted with the water. In the case of solvents such as isopropanol or ethyl acetate a range of 0.1 to 20 ml/g, such as 2 to 10 ml/g and particularly approximately 5 ml/g is suitable, wherein "ml/g" refers to the volume of organic solvent per g of the 4-(3'-chloro-4'-fluoroanilino)-7-methoxy-6-(3-morpholinopropoxy)quinazoline.

When the organic solvent is one with which the 4-(3'-chloro-4'-fluoroanilino)-7-methoxy-6-(3-morpholinopropoxy)quinazoline may form solvates, for example methanol or isopropanol, the slurry process described above should be operated under conditions that repress the formation of solvates with the organic solvent. In the case of isopropanol we have found that a large excess of isopropanol can result in the formation of a metastable isopropanolate dihydrate. The formation of such undesirable solvates is substantially repressed in the slurry process described above by selecting a volume ratio of isopropanol to water of less than 10:1, particularly less than 8:1 and especially less than 5:1. Particularly we have found that a volume ratio of isopropanol to water of from about 1:5 to 5:1, particularly from 1:5 to 2:1 and more particularly about 1:11 to 1:2, favours formation of the Form 5 ZD1839 trihydrate over the metastable isopropanolate.

A single organic solvent may be used or two or more organic solvents, for example a mixture of ethyl acetate and isopropanol (suitably in a volume ratio of approximately 1:1), may be used, together with the water.

Optionally a co-solvent may be used. Suitable co-solvents include, for example, weakly polar organic solvents such as aromatic hydrocarbons (for example toluene), halogeno-(1-6C)alkanes (for example 1,2-dichloroethane) and aliphatic di-(1-6C)alkyl ethers or (4-7C)cyclic ethers (for example tetrahydrofuran). A particular co-solvent is toluene. A suitable ratio by volume of co-solvent (such as toluene) to organic solvent (such as isopropanol) lies within the range 50:1 to 0.05:1, conveniently in the range 10:1 to 0.5:1, and particularly from about 3:1 to 1:1.

As will be appreciated, the slurry of the 4-(3'-chloro-4'-fluoroanilino)-7-methoxy-6-(3-morpholinopropoxy)quinazoline, water and optional organic solvent and co-solvent may be prepared in any order. For example, the starting material may be prepared as a slurry in the organic solvent (and optional co-solvent) followed by addition of the water. Alternatively the starting material may be prepared as a slurry in water followed by addition of the solvent (and co-solvent, if present), or the starting material may be prepared as a slurry directly in the water and organic solvent.

Optionally, one or more seeding crystal(s) of the Form 5 ZD1839 trihydrate may be added to the slurry to further enhance the rate of conversion to the Form 5 ZD1839 trihydrate and/or yield of Form 5 ZD1839 trihydrate. The seeding crystals may be added after or, preferably, prior to contact of the Form 1 ZD1839 polymorph with the water. Suitably the slurry is agitated during the process, for example by stirring.

The process is suitably carried out at about ambient temperature, for example from approximately 15 to 30° C., particularly approximately 20 to 25° C.

The time required for conversion to the Form 5 trihydrate is dependent upon the particular reaction conditions used, such as temperature, presence of an organic solvent and whether seeding crystals are used. Generally, a reaction time of, for example, from 5 minutes to 48 hours is suitable.

The crystalline solid Form 5 ZD1839 trihydrate may be isolated by any conventional method, for example by filtration or centrifugation.

It will be appreciated by the man skilled in the art that the procedures described above may be varied using routine skill and knowledge. For example, provided that a crystalline form of the compound of the Formula I substantially in the form of Form 5 ZD1839 trihydrate is obtained, any of the quantity of the compound 4-(3'-chloro-4'-fluoroanilino)7-methoxy-6-(3-morpholinopropoxy)quinazoline that is treated, the volume of water, the nature and volume of any solvent or co-solvent, the ratio of the component solvents if a solvent mixture is employed and the temperature of the process may be varied.

In a further aspect of the present invention there is provided a process for crystallising (or recrystallising) a compound of the Formula I substantially in the form of Form 5 ZD1839 trihydrate (preferably substantially free of any other ZD1839 solvate or any other form of ZD1839) which comprises the steps:—

(a) dissolving the compound 4-(3'-chloro-4'-fluoroanilino)-7-methoxy-6-(3-morpholinopropoxy)quinazoline in a solvent system comprising water and an organic solvent;

(b) reducing the temperature of the solvent system to induce nucleation;

(c) maintaining the mixture at a temperature below that at which nucleation has commenced; and (d) isolating the crystalline Form 5 ZD1839 trihydrate.

Suitable organic solvents in the solvent system include organic solvents which are: (i) water-soluble at the temperature at which the starting material in step (a) of the process is dissolved; and (ii) organic solvents which, when used in the solvent system, repress the formation of solvates other than the trihydrate. Suitable organic solvents include, for example, weakly polar organic solvents such as aliphatic di-(1-6C) alkyl ethers or (4-7C)cyclic ethers such as tetrahydrofuran, more polar protic solvents, for example (2-6C) alcohols such as ethanol and isopropanol, polar non-protic solvents such as (1-4C) allyl (2-3C)alkanoate esters such as ethyl acetate, aliphatic (3-6C) ketones such as acetone, aliphatic amides such as N,N-dimethylformamide or N-methylpyrrolidin-2-one and nitriles such as acetonitrile. A particular organic solvent is, for example isopropanol. A single organic solvent or a mixture of one or more of the above solvents may be used.

Generally a molar excess of water is used in the solvent system (i.e. the molar ratio of water: 4-(3'-chloro-4'-fluoroanilino)-7-methoxy-6-(3-morpholinopropoxy)quinazoline is at least 3:1). The upper limit of water concentration is not critical, however, generally a large molar excess of water is used. For example the molar ratio of water to 4-(3'-chloro-4'-fluoroanilino)-7-methoxy-6-(3-morpholinopropoxy)quinazoline is suitably from about 3:1 to 1000:1 or more, particularly from about 3:1 to about 400:1.

Optionally, a co-solvent may be used in the solvent system. Suitable co-solvents include, for example, aromatic hydrocarbons such as toluene and aliphatic halogenated hydrocarbons such as halogeno-(1-6C)alkanes, for example 1,2-dichloroethane. A particular organic solvent/co-solvent which may be used in the solvent system is, for example, a mixture of toluene and isopropanol where, for example, the ratio by volume of toluene to isopropanol conveniently lies within the range 5:1 to 0.2:1, more conveniently in the range 2:1 to 0.5:1.

The compound 4-(3'-chloro-4'-fluoroanilino)-7-methoxy-6-(3-morpholinopropoxy)quinazoline may be dissolved in step (a) of the process by heating the compound in the solvent system until substantially all of the compound has dissolved. Conveniently the compound in the solvent system in step (a) of the process is heated at the reflux temperature of the solvent system for sufficient time to completely dissolve the compound. The solution of the compound 4-(3'-chloro-4'-fluoroanilino)-7-methoxy-6-(3-morpholinopropoxy)quinazoline may then be removed from the heat source and allowed to cool to ambient temperature or it may be cooled further, for example to about 0° C. in a bath of ice and water. Alternatively, the solution may be cooled at a controlled rate to about 0° C. A suitable cooling rate is, for example, about 10° C. per hour. It will be appreciated that the nucleation may occur either spontaneously or on adding one or more seed crystals. The crystalline Form 5 ZD1839 trihydrate so obtained may be isolated by any conventional method for example by filtration or centrifugation.

As mentioned herein, under certain conditions it is possible to form a metastable isopropanolate dihydrate form of the compound of Formula I. We have found that when the compound of Formula I is crystallised or recrystallised from a solvent system containing isopropanol, the compound of Formula I may be prepared in high purity substantially as the Form 5 ZD1839 trihydrate and substantially in the absence of isopropanolate solvates by selecting suitable volume ratios of water to isopropanol and/or a suitable co-solvent and/or a suitable cooling rate and/or appropriate seeding to induce nucleation and crystallisation.

In one embodiment of this process, when the solvent system comprises water and isopropanol and optionally toluene co-solvent, a volume ratio of water to isopropanol of from about 1.5:1 to 1:12 (particularly from about 1.3:1 to 1:10, more particularly about 1.2:1 to 1:2 and still more particularly at about 1:1), in conjunction with a slow cooling to induce nucleation of the Form 5 ZD1839 trihydrate gives the Form 5 ZD1839 trihydrate substantially in the absence of other forms of the compound of Formula I, particularly the absence of isopropanolates. A suitable slow cooling rate in this embodiment is, for example, cooling from the reflux temperature of the solvent system to about ambient temperature at a cooling rate of about 10° C. per hour. Alternatively in this embodiment, the solution of the compound 4-(3'-chloro-4'-fluoroanilino)-7-methoxy-6-(3-morpholinopropoxy)quinazoline may be removed from the heat source and allowed to cool to about 30° C. to encourage nucleation of the Form 5 ZD1839 trihydrate. The mixture may be reheated to about 50° C. and then be allowed to cool to ambient temperature or it may be cooled further, for example to about 0° C. in a bath of ice and water. Alternatively, the solution may be cooled from about 50° C. at a controlled rate to about 0° C. A suitable cooling rate is, for example, about 10° C. per hour. Nucleation of the Form 5 ZD1839 trihydrate may also be induced by addition of one or more seed crystals.

The crystalline Form 5 ZD1839 trihydrate: so obtained may be isolated by any conventional method, for example by filtration or centrifugation.

When one or more seed crystals are used to initiate nucleation in the crystallisation/recrystallisation processes described above, the seed crystals are preferably crystals of the Form 5 ZD1839 trihydrate. The seed crystal(s) may be prepared using any suitable method for the preparation of Form 5 ZD1839 trihydrate, for example by slurrying a sample of the Form 1 ZD1839 polymorph in water as hereinbefore described.

It will be appreciated by the man skilled in the art that the procedures described above may be varied using routine skill and knowledge. For example, provided that Form 5 ZD1839 trihydrate is obtained substantially free of any other ZD1839 polymorph or any ZD1839 solvate, any of the quantity of the compound 4-(3'-chloro-4'-fluoroanilino)-7-methoxy-6-(3-morpholinopropoxy)quinazoline that is treated, the nature and volume of the solvent and any co-solvent, the ratio of the component solvents if a solvent mixture is employed, the volume of water used and the ratio of water to solvent and the temperatures of the dissolution and cooling phases may be varied. For example, nucleation of a solution of the compound of the Formula I in a suitable solvent, for example a (2-6C) alcohol such as ethanol in step (b) of the process may be induced by, for example, the evaporation of some of the ethanol solvent, alternatively, nucleation could be induced by the addition of a suitable antisolvent for the compound of Formula I, thereby creating supersaturation and nucleation of the solution from which Form 5 ZD1839 trihydrate crystallises.

The crystallisation process for preparing the Form 5 ZD1839 trihydrate enables the trihydrate to be prepared in high purity, furthermore recrystallisation of the Form 5 ZD1839 trihydrate so obtained may be carried out using the process described above. Recrystallisation offers the possibility for further purifying the material.

We have also found that the Form 5 ZD1839 trihydrate can be readily converted to the Form 1 ZD1839 polymorph. Accordingly, crystallisation of the Form 5 ZD1839 trihydrate and subsequent conversion to the Form 1 ZD1839 polymorph provides a means for preparing the Form 1 ZD1839 polymorph in high purity. Such a process for the preparation of the compound of Formula I substantially in the form of Form 1 ZD1839 polymorph (preferably substantially free of any other ZD1839 solvate or any other form of ZD1839) provides a further aspect of the present invention and comprises, for example:—

Conversion Process 1

(a) washing compound of Formula I substantially in the form of Form 5 ZD1839 trihydrate with a solvent or solvent mixture substantially to remove water; and (b) isolating the Form 1 ZD1839 polymorph so formed; or Conversion Process 2 by heating compound of Formula I substantially in the form of Form 5 ZD1839 trihydrate for a sufficient time and at sufficient temperature to drive off water and effect transformation to Form 1 ZD1839 polymorph.

In conversion process 1, a suitable solvent includes, for example, water-miscible organic solvents in which the compound of Formula I is sparingly soluble at the washing temperature. Examples of suitable solvents include, weakly polar organic solvents such as aliphatic di-(1-6C)alkyl ethers or (4-7C)cyclic ethers such as tetrahydrofuran, more polar protic solvents, for example (2-6C) alcohols such as ethanol and isopropanol, polar non-protic solvents such as (1-4C)alkyl (2-3C)alkanoate esters such as ethyl acetate and nitriles such as acetonitrile. Mixtures of such solvents may also be employed. A particular solvent is isopropanol and/or ethyl acetate.

As described above in relation to the conversion of the Form 3 ZD1835 DMSO solvate, it is to be understood that the 'washing' step requires a suitable period of time to effect conversion to the Form 1 ZD1839 polymorph. A suitable contact time between the solid and washing solvent is in the range of about 5 minutes to 1 or more hours. More conveniently, the contact time is in the range of about 30 minutes to about 2 hours, for example about 1 hour. Conveniently, a slurry of the solid and the washing solvent is prepared. Conveniently, the slurry is stirred to improve contact between the washing solvent and the crystals of solid. The washing solvent may be warmed, for example to a temperature of about 30 to 50° C., however, generally washing at about ambient temperature is sufficient to effect conversion to the Form 1 ZD1839 polymorph.

In a particular embodiment of conversion process (a), the Form 5 ZD1839 trihydrate is washed with isopropanol, suitably by stirring a slurry of the Form 5 ZD1839 trihydrate in isopropanol for approximately 5 minutes to 1 hour or more, particularly about 30 minutes. Conveniently, the isopropanol wash is carried out at about ambient temperature. The resulting solid is then isolated, for example as hereinbefore described (such as by filtration) and the isolated solid is washed for a second time with an additional organic solvent. Suitably the additional organic solvent is one that is more volatile than the isopropanol, for example ethyl acetate. The second wash is, for example, carried out by stirring the solid as a slurry in the additional organic solvent. Suitably the second wash is carried out at approximately ambient temperature and for sufficient time to substantially remove any remaining water from the solid material, for example from 5 minutes to 1 hour or more, particularly about 30 minutes. The resulting Form 1 ZD1839 polymorph may then be isolated using conventional techniques as hereinbefore described.

Optionally, the material isolated following the solvent washing step(s) in conversion process 1 is dried to ensure complete removal of water and conversion to the desired Form 1 ZD1839 polymorph. A suitable drying temperature is, for example, from 45 to 150° C., particularly from 60 to 80° C. As will be recognised, the drying time will be dependent upon, amongst other things, the amount of material to be dried, and the particular drying method used. Generally a drying time of 30 minutes to 100 hours, for example 1 to 30 hours is sufficient. Conveniently the drying is performed under an inert atmosphere, for example by passing a stream of warm inert gas such as nitrogen over or through the material or by drying under vacuum.

Conversion process 2 is suitably carried out by heating the Form 5 ZD1839 trihydrate at a temperature of from 50 to 150° C., particularly from 80 to 140° C., more particularly from 120 to 130° C. The heating time required is dependant on, amongst other things, the size of the sample and the heating method employed. Generally a heating time of from 5 minutes to 100 hours, suitably 1 to 30 hours, is sufficient to convert the Form 5 ZD1839 trihydrate to Form 1 ZD1839 polymorph. The Form 5 ZD1839 trihydrate may be heated using conventional techniques, for example in a suitable oven or vacuum oven or in a conventional drying system such as a fluid bed dryer.

It is thought that the heating of Form 5 ZD1839 trihydrate may result in the transient formation of one or more metastable forms of the compound of the Formula I, including a metastable anhydrous ZD1839 polymorph. Any such metastable forms are less stable that the Form 1 ZD1839 polymorph and continued heating results in transformation of the transient metastable forms to the more stable Form 1 ZD1839 polymorph. Accordingly, the heating step in conversion process 2 should be continued for sufficient time and at sufficient temperature to ensure substantially complete conversion to the desired Form 1 ZD1839 polymorph. By substantially complete conversion is meant that at least 80% of the compound of the Formula I is in the form of Form 1 ZD1839 polymorph and less than 20% of the compound of the Formula I is in the form of any other ZD1839 solvate or any other ZD1839 polymorph. Particularly at least 90% and, in particular, at least 95% of the compound of the Formula I is in the form of Form 1 ZD1839 polymorph. The degree of conversion to the required Form 1 ZD1839 polymorph may be assessed using routine techniques, for example XRPD as described herein and the heating temperature and/or time adjusted accordingly.

The invention is illustrated hereinafter by means of the following Examples, data and Figures in which:—

(i) X-ray diffraction patterns were obtained using a Siemens D5000 machine in θ-θ configuration over the scan range 2° 2θ to 40° 2θ with 4 seconds exposure per 0.02° 2θ increment. The X-rays were generated by a copper long-fine focus tube operated at 40 kV and 40 mA. The wavelength of the X-rays was 1.5406 Å. The examinations were carried out in Bragg-Brentano configuration whereby the X-ray beam was passed through an Automatic Variable Divergence Slit at V20. The sample was prepared by gently breaking up crystal aggregates using an agate pestle and mortar. The sample was filled into a standard holder (having a flat lip) and compressed flush to the lip with a glass microscope slide. The sample was spun at 30 revolutions per minute (rpm) to improve counting statistics. The reflections are quoted as their centroid values (calculated by a computer package such as DIFFRAC/AT). It should be realised that analysis of samples with grains above 30 microns in size and non-unitary aspect ratios may affect the relative intensity of peaks. The skilled person will also realise that the position of reflections is affected by the precise height at which the sample sits in the diffractometer and the zero calibration of the diffractometer. The surface planarity of the sample may also have a small effect. Hence the diffraction pattern data presented are not to be taken as absolute values.

(ii) Melting points and TGA in Examples 1 to 5 were determined using Perkin Elmer Pyris 1 DSC/TGA equipment. The pan type was aluminium (50 μl size) with a pierced lid. The sample weight was approximately 1 to 4 mg. Melting point and weight loss during heating on the Form 5 ZD1839 trihydrate in Examples 6 to 8 were determined using DSC and TGA respectively using Mettler DSC820E and TG851 with TSO891RO robotic systems. The pan type was aluminium (40 μl size) with a pierced lid. The procedures were carried out under a flow of nitrogen gas (100 ml/min) and the temperature range studied was 40° C. to 300° C. at a constant rate of temperature increase of 10° C. per minute. The skilled person will realise that the precise value of the melting point will be influenced by the purity of the compound, the sample weight, the heating rate and the particle size. It will therefore be appreciated that alternative readings of melting point may be given by other types of equipment or by using conditions different to those described. For the TGA, each sample (approximately 2 mg) was heated in an open ceramic crucible from 15° C. to 300° C. at a rate of 10° C. per minute.

(iii) DRIFT spectroscopy was recorded on a Nicolet 20SXC spectrometer using a 2% w/w dispersion of the sample in powdered potassium bromide over the frequency range 4000 to 400 cm$^{-1}$.

EXAMPLE 1

Figure 1:
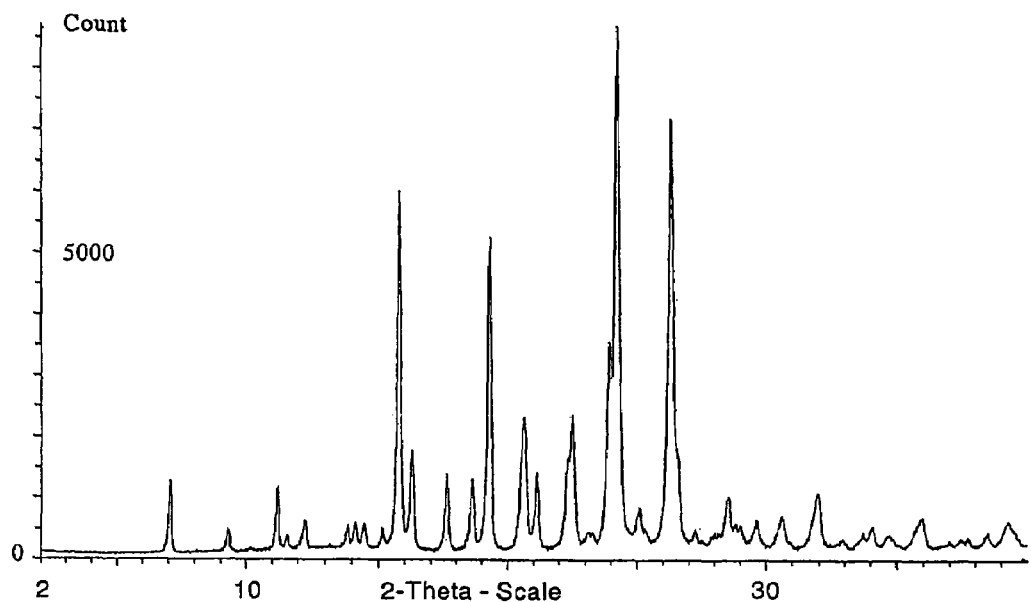
FIG. 1 shows the X-ray powder diffraction pattern for Form 1 ZD1839 polymorph with the 2θ values plotted on the horizontal axis and the relative line intensity (Count) plotted on the vertical axis.
Figure 2:
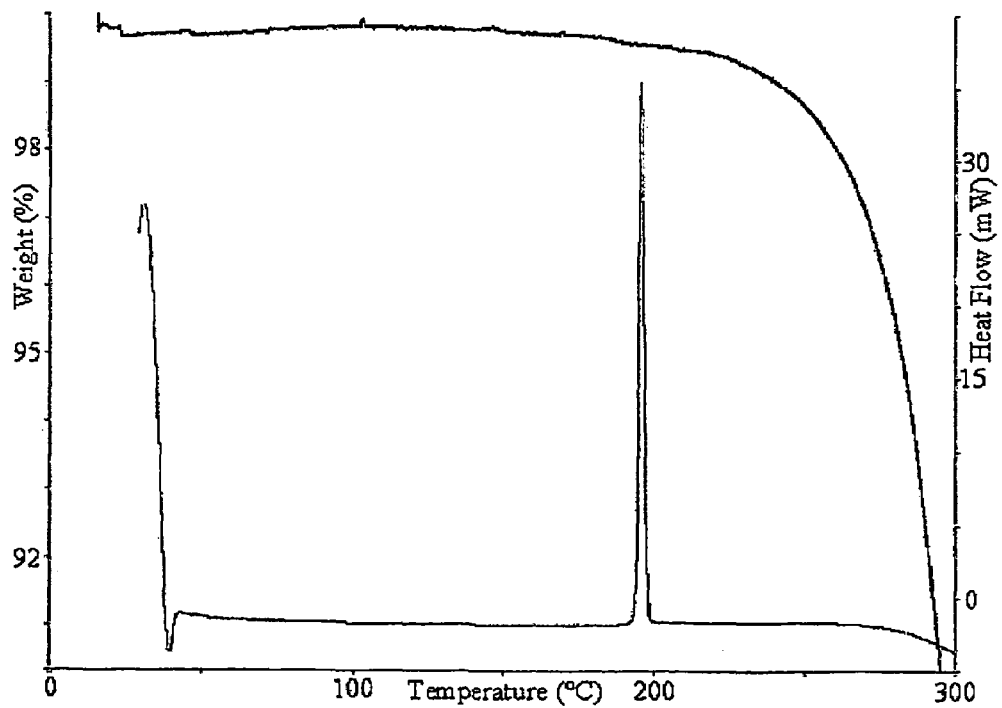
FIG. 2 shows the DSC thermogram and TGA trace for Form 1 ZD1839 polymorph with temperature (° C.) plotted on the horizontal axis and endothermic heat flow (milliWatts (mW)) and sample weight (percentage of initial weight) plotted on the two vertical axes.
Figure 3:
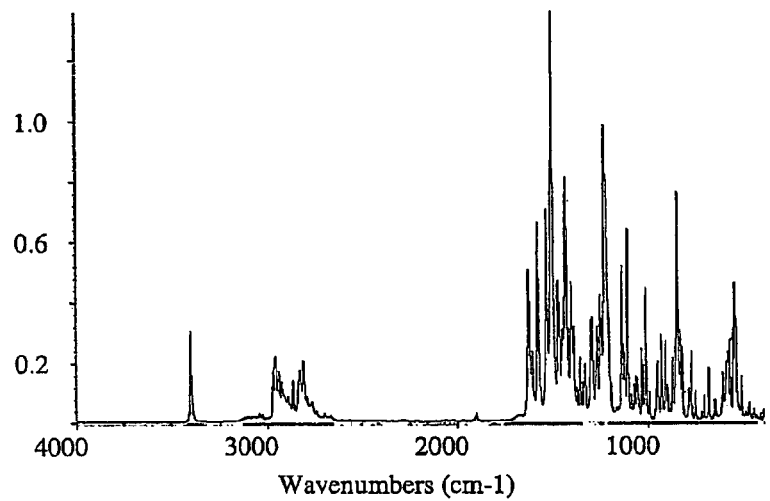
FIG. 3 shows the DRIFT spectrum for Form 1 ZD1839 polymorph with the frequency range 4000 to 400 cm$^{-1}$ plotted on the horizontal axis and absorbance plotted on the vertical axis.
Figure 4:
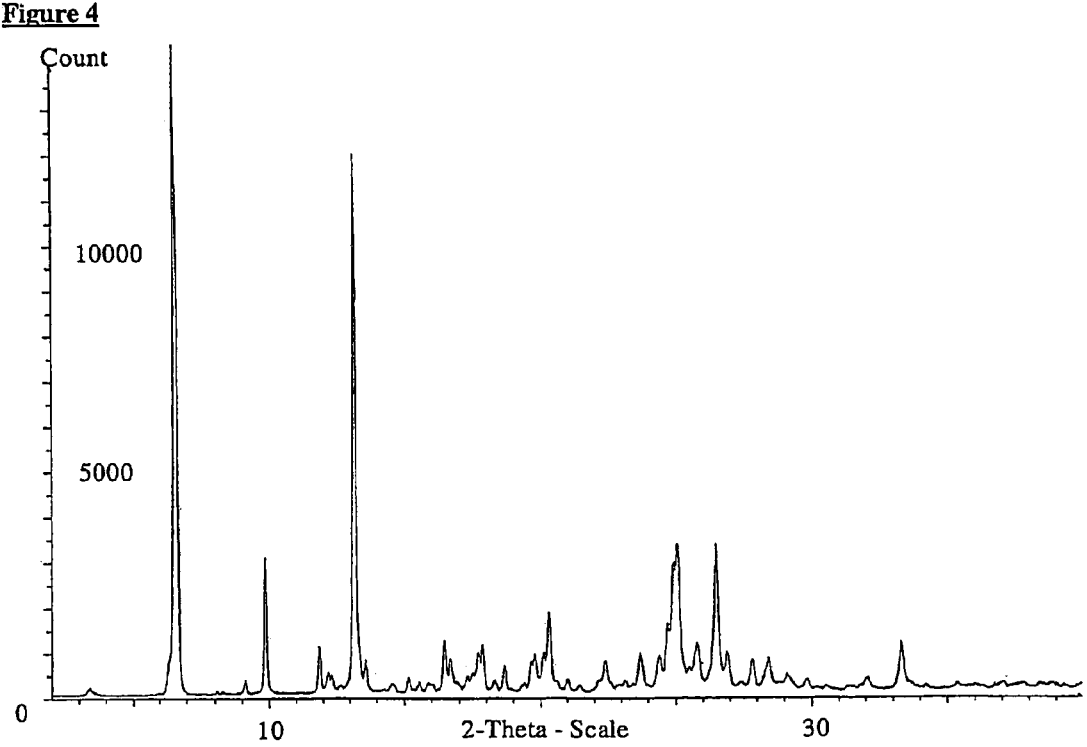
FIG. 4 shows the X-ray powder diffraction pattern for Form 2 ZD1839 MeOH solvate with the 2θ values plotted on the horizontal axis against an expanded scale of relative line intensity values (Count) plotted on the vertical axis.
Figure 5:
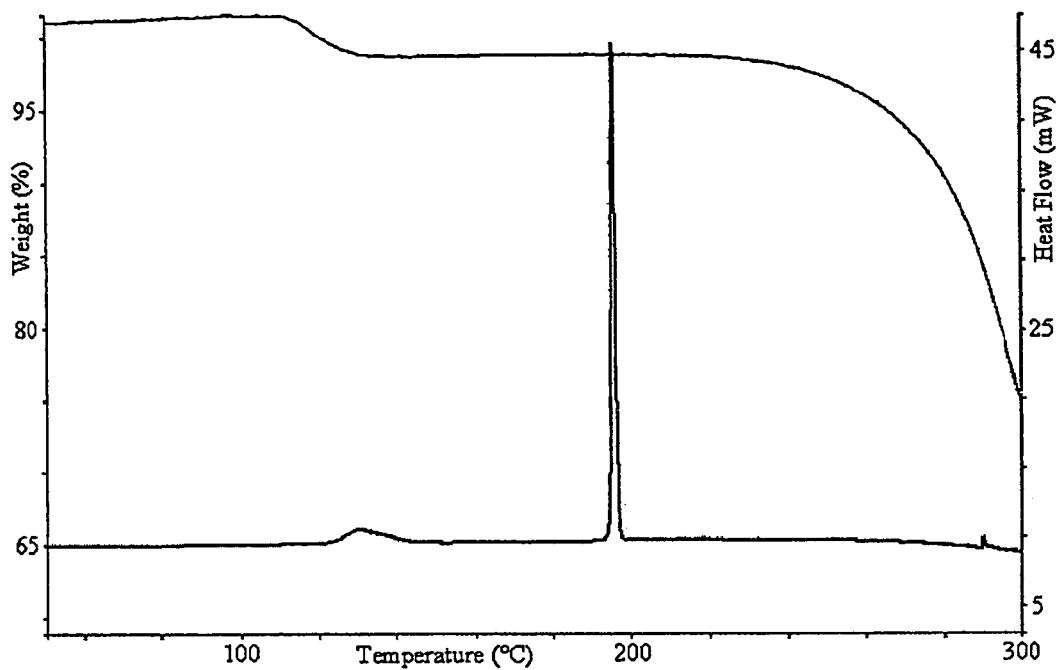
FIG. 5 shows the DSC thermogram and TGA trace for Form 2 ZD1839 MeOH solvate with temperature (° C.) plotted on the horizontal axis and endothermic heat flow (mW) and sample weight (percentage of initial weight) plotted on the two vertical axes.
Figure 6:
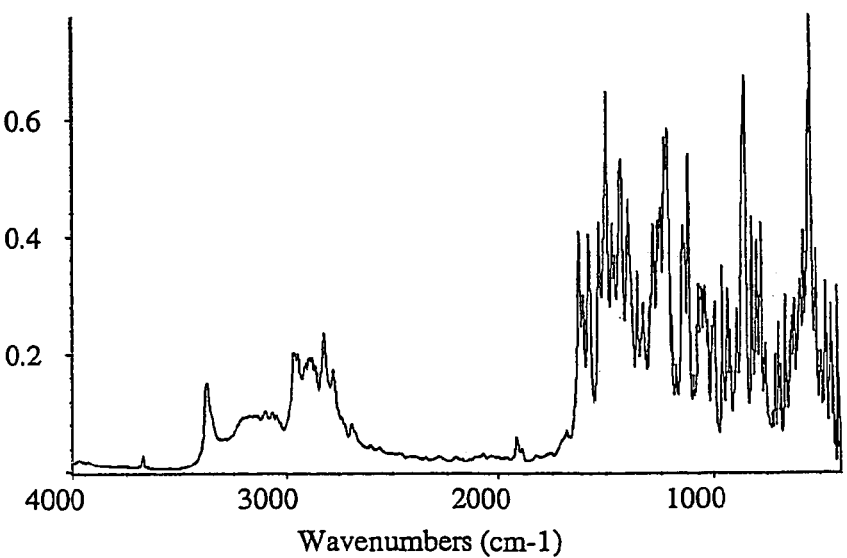
FIG. 6 shows the DRIFT spectrum for Form 2 ZD1839 MeOH solvate.

Form 3 ZD1839 DMSO Solvate 4-(3'-chloro-4'-fluoroanilino)-7-methoxy-6-(3-morpholinopropoxy)quinazoline mono-solvate with dimethyl sulphoxide With warming to about 75° C., 4-(3'-chloro-4'-fluoroanilino)-7-methoxy-6-(3-morpholinopropoxy)quinazoline (204 kg) was dissolved in a mixture of ethyl acetate (1021 liters) and dimethyl sulphoxide (181 liters) containing diatomaceous earth filter aid (5 kg). The resultant mixture was filtered and ethyl acetate (78 liters) was used to wash the filter aid solid. The filtrate and washings were combined and cooled initially to about 10° C. The mixture was then heated to about 40° C. for 1 hour. The warm mixture was cooled to 0° C. at a rate of about 10° C. per hour. The resultant solid was collected by filtration. There was thus obtained Form 3 ZD1839 DMSO solvate as shown by XRPD and DSC analysis.

The 4-(3'-chloro-4'-fluoroanilino)-7-methoxy-6-(3-morpholinopropoxy)quinazoline used as a starting material is disclosed in International Patent Application WO 96/33980 within Examples 1 and 10. The material may also be obtained as described in Example 4 hereinafter.

EXAMPLE 2

Form 2 ZD1839 MeOH Solvate 4-(3'-chloro-4'-fluoroanilino)-7-methoxy-6-(3-morpholinopropoxy)quinazoline hemi-methanolate A mixture of 4-(3'-chloro-4'-fluoroanilino)-7-methoxy-6-(3-morpholinopropoxy)quinazoline (25 g) and methanol (250 ml) was stirred and heated to reflux for 30 minutes to ensure that the solid was fully in solution. The solution was cooled down at a rate of about 10° C. per hour from the reflux temperature to a temperature of 0° C. and then held at 0° C. for 1 hour. The resultant crystalline solid was collected by suction filtration and pulled dry on the filter. XRPD analysis and the DSC thermogram and TGA trace showed that the Form 2 ZD1839 MeOH solvate so obtained had about 2 equivalents of ZD1839 to about 1 equivalent of methanol, i.e. the material was approximately a hemi-solvate.

EXAMPLE 3

Process of Conversion of Form 3 ZD1839 DMSO Solvate to Form 1 ZD1839 Polymorph

Form 3 ZD1839 DMSO solvate (from Example 1) was washed with ethyl acetate (581 litres). The washed solid was mixed with ethyl acetate (895 liters) and the resultant slurry was stirred and heated to 34° C. for about 1 hour. The mixture was then cooled to 0° C. and held at that temperature for 2 hours to allow the conversion to proceed. The resultant solid was separated by filtration, washed with ethyl acetate (580 liters) and dried in a flow of warm nitrogen gas (60° C.). There was thus obtained Form 1 ZD1839 polymorph (161 kg) as shown by XRPD and DSC analysis.

EXAMPLE 4

Form 1 ZD1839 Polymorph 4-(3'-chloro-4'-fluoroanilino)-7-methoxy-6-(3-morpholinopropoxy)quinazoline Whilst maintaining the temperature of the reaction mixture at about 50° C., phosphorus oxychloride (365 kg) was added to a stirred slurry of 7-methoxy-6-(3-morpholinopropoxy)-3,4-dihydroquinazolin-4-one (International Patent Application WO 01/04102 within Example 25; 220 kg), triethylamine (105 kg) and toluene (1790 liters). The resultant mixture was stirred at about 50° C. for 5 hours to complete the formation of 4-chloro-7-methoxy-6-(3-morpholinopropoxy)quinazoline.

The resultant stirred slurry was cooled to about 0° C. and isopropanol (527 liters) was added whilst the temperature of the reaction mixture was maintained between 0° and 5° C. The reaction mass was then warmed to about 20° C. and held at that temperature for about 1 hour. A solution of 3-chloro-4-fluoroaniline (168 kg) in isopropanol (228 liters) was added and the resultant reaction mixture was stirred and warmed to about 66° C. and held at that temperature for about 1 hour. The mixture was stirred and cooled to about 30° C. and isopropanol (662 liters) and water (1486 liters) were added in turn. A mixture of aqueous sodium hydroxide liquor (47% w/w, 755 kg) and water (40 liters) was added portionwise to the stirred reaction mixture. The resultant mixture was warmed to about 64° C. and the two liquid phases were allowed to separate. The lower aqueous layer was run off. The remaining organic phase was initially cooled to about 30° C., warmed to about 50° C. and finally cooled to about 20° C. at a rate of about 10° C. per hour. The resultant solid was collected by filtration. The solid so obtained was washed with isopropanol by preparing a slurry of the material in isopropanol that was stirred for about 30 minutes. The resultant solid was isolated by filtration. The solid so obtained was washed with ethyl acetate by preparing a slurry of the material in ethyl acetate that was stirred for about 30 minutes. The resultant solid was isolated by filtration. The ethyl acetate wash was repeated. The resultant solid was dried with warm nitrogen gas (60° C.). There was thus obtained 4-(3'-chloro-4'-fluoroanilino)-7-methoxy-6-(3-morpholinopropoxy)quinazoline in the form of Form 1 ZD1839 polymorph (224 kg) as shown by XRPD and DSC analysis.

EXAMPLE 5

Single Crystal X-Ray Data of Form 1 ZD1839 Polymorph

Well-shaped single crystals of Form 1 ZD1839 polymorph were obtained by slow evaporation at ambient temperature of a solution of the compound of the Formula I in absolute ethanol. In order to preclude the influence of air during the data collection, the selected single crystal was protected with glue. The X-ray diffraction intensities were collected at 200° K using graphite monochromatised MoK($\alpha$) radiation and a double-pass method on a Kappa Charged Coupled Device (CCD) single-crystal X-ray diffractometer equipped with a κ-axis goniometer and an image CCD area detector (Nonius BV; Kappa-CCD Server Software, Nonius, Delft, The Netherlands). The diffraction raw data were processed using the Denzo-SMN (Small Molecule Nonius) computer program package, (Z Otwinowski & W Minor, Processing of X-ray Diffraction Data Collected in Oscillation Mode, *Methods in Enzymology*, 1997, 276, 302-326) converting the information from the digital image frame to a computer file containing h, k and l indices, background and Lp corrected intensities of the diffraction spots and estimate of errors. In order to cover the diffraction spots (reflections) within the Ewald sphere, 478 image frames were recorded with a crystal-camera distance of 35 mm with a step interval of 1°. Each frame was irradiated twice in order to discriminate the spare spots generated by cosmic radiation. Accurate unit-cell dimensions were obtained as a result of the real-space vector search that indexed reflections. Three linearly independent vectors with minimal determinant (unit-cell volume) were used to define the cell parameters within the Denzo-SMN package. The structure was solved with direct methods using the SIR92 computer program package for the automatic solution of crystal structures from X-ray diffraction data (A Altomare, et al., 1992) and refined with full-matrix least-squares technique. The refinements were based on F, exploiting the programs within the MaXus software package (S MacKay et al., 1997 via the Chemistry Department, Glasgow University, Scotland; a computer program for solving, refining and publishing crystal structures from X-ray diffraction data; developed for Mac Science Co., Japan and Nonius, The Netherlands) and the Platon software package (A Spek et al., 1992, a computer program developed for the generation and analysis of stereochemical and molecular geometry data). In the final step of the refinement calculations, all non-hydrogen atoms were allotted with anisotropic thermal displacement factors. The hydrogen atom positions were calculated geometrically and fixed at relevant positions, 0.96 Å from the parent atom. The isotropic displacement factors of all hydrogen atoms were fixed to 0.05 Å$^2$. In the full-matrix least squares refinements 281 variables were refined against 3184 reflections (with $F^2_o > 3\sigma F^2_o$). Further, the final reliability values converged to R=0.0404 and Rw=0.0440. Relevant crystal data together with experimental details and structural refinement parameters are summarised in Table A:1 and atomic coordinates are provided in Table A:2.

TABLE A:1

Experimental and Refinement Calculation data for Form 1 ZD1839 polymorph

| Crystal data | |
|---|---|
| $C_{22}H_{24}ClFO_3N_4$ | MoK($\alpha$) radiation: |
| $M_r$ = 446.91 | $\lambda$ = 0.71073 Å |
| Crystal System: Triclnic | Space group: P-1 |
| Unit-cell parameters: | average values from image indexed reflections |
| a = 8.876(1) Å | $\alpha$ = 93.51(1)° |
| b = 9.692(1) Å | $\beta$ = 97.36(1)° |
| c = 12.543(1) Å | $\gamma$ = 101.70(1)° |
| V = 1043.6(2) Å$^3$ | crystal shape: needle |
| Z = 2 | 0.14 × 0.14 × 0.29 mm |
| $D_x$ = 1.4222(3) Mg m−3 | colourless |
| T = 200 K | $\mu$ = 2.2 cm−1 |
| hkl-range: | −10 < h < 11, −9 < k < 12, −16 < l < 16 |
| F(000) = 468.0 electrons | |
| Data collection | |
| Nonius BV KappaCCD Diffractometer | |
| Number of collected frames: | 478 |
| Number of repeats: | 1 |
| Distance: crystal-detector | $D_x$ = 35 mm |
| Phi-rotation step | 1 |
| Exposure time: | 15 sec/frame |
| Resolution: | 0.66 Å |
| Covered θ-range: | 1-27.5 |
| Total number of measured reflections: | 4646 |
| Number of unique observed reflections, $F^2_o > 3\sigma(F^2_o)$: | 3184 |
| Absorption correction: | none |
| Extinction parameter (Zachariasen, 1970) | 9.9479 exp −3 |
| Refinement | |
| MaXus (1997) | $(\Delta/\sigma)_{max}$ = 0.0006 |
| Refinement on F | $(\Delta/\sigma)_{mean}$ = 0.0001 |
| R = 0.0404 | $\Delta\rho_{max}$ = 0.21 e Å$^{-3}$ |
| Rw = 0.0440 | $\Delta\rho_{min}$ = −0.22 eÅ$^{-3}$ |
| Weighting scheme: | w = 1/($\sigma^2 F_o^2$ + (0.0300)$F^2$) |
| Atomic scattering factors: | maXus (1997) |
| 281 parameters | |
| Atomic displacement factors: | |
| non-H atoms | anisotropic |
| H atoms | $U_{(iso)}$ = 0.05 Å$^2$ |

TABLE A:2

Final Coordinates and Equivalent Isotropic Displacement Parameters of the non-Hydrogen atoms for Form 1 ZD1839 polymorph.

| Atom  | x          | y          | z           | U(eqv) [Å²] |
|-------|------------|------------|-------------|-------------|
| Cl(19)| 0.36275(4) | 0.84068(3) | 0.42511(2)  | 0.0619(1)   |
| F18   | 0.39031(7) | 1.08739(6) | 0.29892(5)  | 0.0549(2)   |
| O20   | 0.93090(8) | 0.14285(6) | −0.02633(5) | 0.0390(2)   |
| O22   | 0.86297(7) | 0.20079(6) | 0.16029(4)  | 0.0340(2)   |
| O29   | 1.25684(7) | 0.45236(6) | 0.64985(4)  | 0.0370(2)   |
| N1    | 0.75916(9) | 0.54835(8) | −0.16301(6) | 0.0373(3)   |
| N3    | 0.65090(9) | 0.69616(7) | −0.04568(6) | 0.0351(3)   |
| N11   | 0.62866(9) | 0.64913(7) | 0.13265(5)  | 0.0319(3)   |
| N26   | 1.09809(9) | 0.28952(7) | 0.45555(5)  | 0.0307(3)   |
| C2    | 0.69633(12)| 0.65563(10)| −0.13936(7) | 0.0395(3)   |
| C4    | 0.67182(10)| 0.61580(8) | 0.03459(7)  | 0.0285(3)   |
| C5    | 0.73888(10)| 0.49402(8) | 0.02221(6)  | 0.0271(3)   |
| C6    | 0.76526(10)| 0.40484(8) | 0.10497(7)  | 0.0291(3)   |
| C7    | 0.83115(10)| 0.29184(8) | 0.08601(7)  | 0.0283(3)   |
| C8    | 0.87139(10)| 0.26072(9) | −0.01814(7) | 0.0293(3)   |
| C9    | 0.84831(10)| 0.34655(9) | −0.09798(7) | 0.0312(3)   |
| C10   | 0.78163(10)| 0.46535(8) | −0.07936(7) | 0.0289(3)   |
| C12   | 0.56635(10)| 0.76385(8) | 0.16763(7)  | 0.0295(3)   |
| C13   | 0.56934(11)| 0.88739(9) | 0.11619(7)  | 0.0355(3)   |
| C14   | 0.50760(12)| 0.99477(9) | 0.15990(7)  | 0.0383(3)   |
| C15   | 0.44717(11)| 0.98025(9) | 0.25485(8)  | 0.0367(3)   |
| C16   | 0.44402(11)| 0.85905(9) | 0.30697(7)  | 0.0350(3)   |
| C17   | 0.50256(11)| 0.75092(9) | 0.26345(7)  | 0.0327(3)   |
| C21   | 0.97517(12)| 0.10326(10)| −0.12755(7) | 0.0414(3)   |
| C23   | 0.83007(11)| 0.23029(9) | 0.26738(7)  | 0.0323(3)   |
| C24   | 0.88933(11)| 0.12432(9) | 0.33581(7)  | 0.0346(3)   |
| C25   | 1.06324(12)| 0.16967(9) | 0.37237(7)  | 0.0374(3)   |
| C27   | 1.25450(12)| 0.37519(10)| 0.46087(7)  | 0.0411(3)   |
| C28   | 1.28014(12)| 0.49842(10)| 0.54589(8)  | 0.0426(4)   |
| C30   | 1.10343(12)| 0.36784(10)| 0.64376(7)  | 0.0413(3)   |
| C31   | 1.07840(11)| 0.24200(10)| 0.56203(7)  | 0.0381(3)   |

Temperature factor of the form: T = exp[−2π²U], U = U(eqv) where U(eqv) = 1/3 Σ(i)Σ(j){U(ij)a(i)a(j)a(i)a(j)}

EXAMPLE 6

Form 5 ZD1839 Trihydrate: Prepared by Slurry Process in a Solvent System Containing Water A mixture of 4-(3'-chloro-4'-fluoroanilino)-7-methoxy-6-(3-morpholinopropoxy)quinazoline (1 g; Form 1 ZD1839 polymorph, prepared as described in Example 4), isopropanol (5 ml), toluene (10 ml) and water (5 ml) was stirred as a slurry at room temperature for 18 hours. The resultant crystalline solid was collected by suction filtration and pulled dry on the filter. Analysis of the XRPD, DSC thermogram and TGA trace on the resultant product confirmed the product to be Form 5 ZD1839 trihydrate, which contained 1 equivalent of ZD1839 to 3 equivalents of water. The stoichiometry of the trihydrate was confirmed by single-crystal studies and Karl Fischer water analysis as described herein.

Using an analogous procedure to that described above, the organic solvent/co-solvent systems shown in Table 2 were used to prepare Form 5 ZD1839 trihydrate:

TABLE 2

| Example | Water    | Organic solvent     | Co-solvent          |
|---------|----------|---------------------|---------------------|
| 6.1     | 10 ml/g  | isopropanol (5 ml/g)|                     |
| 6.2     | 10 ml/g  | isopropanol (10 ml/g)|                    |
| 6.3     | 1 ml/g   | isopropanol (5 ml/g)| ethyl acetate (5 ml/g) |

"ml/g" in Table 2 refers to the volume of water/solvent per g of 4-(3'-chloro-4'-fluoroanilino)-7-methoxy-6-(3-morpholinopropoxy)quinazoline The 4-(3'-chloro-4'-fluoroanilino)7-methoxy-6-(3-morpholinopropoxy)quinazoline starting material used in Examples 6 may also be prepared using the methods disclosed in International Patent Application WO 96/33980 within Examples 1 and 10.

EXAMPLE 7

Form 5 ZD1839 Trihydrate: Prepared by Crystallisation from a Solvent System Containing Water Water (900 ml) and isopropanol (720 ml) were added to 4-(3'-chloro-4'-fluoroanilino)-7-methoxy-6-(3-morpholinopropoxy)quinazoline (60 g). The mixture was stirred and heated to reflux (approximately 82° C.). Additional isopropanol (90 ml) was added to achieve complete dissolution of the solid. The solution was maintained at reflux for a further 2 hours before cooling to ambient temperature over approximately 6 hours. The resulting Form 5 ZD1839 trihydrate was formed as crystalline needles and isolated by filtration.

Solid collected 65.2 g, 97% as trihydrate, confirmed by XRPD, water content was measured to be 10.98% by Karl Fischer titration (10.78% theoretical for trihydrate). Weight loss by TGA was 10.67% occurring between 25 and 105° C.

EXAMPLE 8

Form 5 ZD1839 Trihydrate: Large Scale Synthesis

The process in Example 4 was repeated except that following the cooling of the organic phase to about 30° C., warming to about 50° C. and cooling to about 20° C. at a rate of about 10° C. per hour, the resultant solid was collected by filtration. XPD analysis of the material collected on the filter showed it was Form 5 ZD1839 trihydrate. Further confirmation that the material obtained was the trihydrate were provided by DSC, TGA and Karl Fischer titration.

The Form 5 ZD1839 trihydrate isolated on the filter may be washed with a suitable solvent that will not displace the water of crystallisation, for example cold toluene (suitably at a temperature of 0 to 15° C.). The washed Form 5 ZD1839 trihydrate may then be dried under conditions which do not drive off the water of crystallisation, for example by drying at a low temperature, for example at ambient temperature.

EXAMPLE 9

Form 5 ZD1839 Trihydrate: Single Crystal Analysis

Well-shaped single crystals of Form 5 ZD1839 trihydrate were obtained by slow evaporation at room temperature from an ethanol and water solution of 4-(3'-chloro-4'-fluoroanilino)-7-methoxy-6-(3-morpholinopropoxy)quinazoline. In order to preclude the influence of air during the data collection, the selected single crystal was protected with glue. The X-ray diffraction intensities were collected at 298° K on a Kappa Charged Coupled Device (CCD) single-crystal X-ray diffractometer equipped with graphite monochromatised MoK(α) radiation (Nonius BV; Kappa-CCD Server Software, Nonius, Delft, The Netherlands). The single crystal data was generated and analysed using an analogous method to that described in Example 5 except that during collection of the diffraction data in order to cover the diffraction spots (reflections) within the Ewald sphere, 251 image frames were recorded with a crystal-camera distance of 40 mm with a step interval of 1°. Each frame was irradiated twice, 20 sec/frame, in order to discriminate the spare spots generated by cosmic radiation.

Additionally, in the full-matrix least squares refinements variables were refined against 1504 reflections (with $F^2_o > 3\sigma F^2_o$). Further, the final reliability values converged to R=0.0468 and Rw=0.0526. Relevant crystal data together with experimental details and structural refinement parameters are summarized in Table B:1 and atomic coordinates are provided in Table B:2.

TABLE B:1

Experimental and Refinement Calculation data for ZD1839 trihydrate

Crystal data $C_{22}H_{24}ClFO_3N_4 \cdot 3H_2O$
$M_r = 446.91 + 54.06$
Crystal System: Monoclinic
Unit-cell parameters:

a = 14.405(1) Å
b = 24.891(1) Å
c = 6.811(1) Å
V = 2440.4(4) Å$^3$
Z = 4
$D_x$ = 1.364(1) Mg m−3
T = 298 K
hkl-range:

MoK($\alpha$) radiation:
$\lambda = 0.71073$ Å
Space group: P2$_1$/c
average values from image indexed reflections $\alpha = 90°$
$\beta = 92.18(1)°$
$\gamma = 90°$
crystal shape: needle
0.06 × 0.06 × 0.57 mm
colourless
$\mu = 2.09$ cm$^{-1}$
−17 < h < 17, −30 < k < 30, −8 < l < 8

F(000) = 1056.0 electrons
Data collection
Nonius BV KappaCCD Diffractometer

| | |
|---|---|
| Number of collected frames: | 251 |
| Number of repeats: | 1 |
| Distance: crystal-detector | $D_x$ = 40 mm |
| Phi-rotation step | 1 |
| Exposure time: | 20 sec/frame |
| Resolution: | 0.64 Å |
| Covered θ-range: | 1-27.5 |
| Total number of measured reflections: | 4909 |
| Number of unique observed reflections, $F^2_o > 3\sigma(F^2_o)$: | 1504 |
| Absorption correction: | none |
| Extinction parameter (Zachariasen, 1970) | 14.898 exp$^{-3}$ |

Refinement

MaXus (1997)
Refinement on F
308 parameters/1504 reflections
R = 0.0468
Rw = 0.0526
Weighting scheme:
Atomic scattering factors:
Atomic displacement factors:

$(\Delta/\sigma)_{max} = 0.0003$
$(\Delta/\sigma)_{mean} = 0.0000$ $\Delta\rho_{max} = 0.25$ e Å$^{-3}$
$\Delta\rho_{min} = -0.28$ eÅ$^{-3}$
w = 1/($\sigma^2 F_o^2 + (0.0300)F^2$)
maXus (1997)

non-H atoms    anisotropic
H atoms        $U_{(iso)} = 0.05$ Å$^2$

TABLE B:2

Final Coordinates and Equivalent Isotropic Displacement Parameters of the non-Hydrogen atoms for: ZD1839 trihydrate.

| Atom | x | y | z | U(eqv) [Å$^2$] |
|---|---|---|---|---|
| Cl(19) | 1.02030(13) | 0.20446(10) | 0.5962(3) | 0.1013(10) |
| F18 | 1.0862(3) | 0.1382(2) | 0.9224(6) | 0.103(2) |
| O20 | 0.2787(3) | 0.23699(19) | 0.8144(5) | 0.0504(19) |
| O22 | 0.3532(3) | 0.1444(2) | 0.8396(6) | 0.0472(17) |
| O29 | 0.0649(3) | −0.0199(2) | 0.2566(8) | 0.081(3) |
| N1 | 0.5742(4) | 0.3253(2) | 0.8980(6) | 0.039(2) |
| N3 | 0.7134(4) | 0.2721(3) | 0.9225(7) | 0.042(2) |
| N11 | 0.7091(4) | 0.1797(2) | 0.9301(6) | 0.042(2) |
| N26 | 0.2218(3) | 0.0310(2) | 0.4457(7) | 0.0407(19) |
| C2 | 0.6650(6) | 0.3177(3) | 0.9148(8) | 0.045(3) |
| C4 | 0.6632(5) | 0.2273(3) | 0.9166(8) | 0.035(3) |
| C5 | 0.5639(5) | 0.2278(3) | 0.8976(7) | 0.031(3) |
| C6 | 0.5077(5) | 0.1816(3) | 0.8838(8) | 0.036(3) |
| C7 | 0.4146(5) | 0.1862(3) | 0.8579(7) | 0.034(3) |
| C8 | 0.3730(5) | 0.2381(3) | 0.8462(7) | 0.036(3) |
| C9 | 0.4262(5) | 0.2830(3) | 0.8622(8) | 0.035(3) |
| C10 | 0.5231(5) | 0.2786(3) | 0.8872(7) | 0.035(3) |

TABLE B:2-continued

Final Coordinates and Equivalent Isotropic Displacement Parameters of the non-Hydrogen atoms for: ZD1839 trihydrate.

| Atom | x | y | z | U(eqv) [Å$^2$] |
|---|---|---|---|---|
| C12 | 0.8070(5) | 0.1726(3) | 0.9321(9) | 0.042(3) |
| C13 | 0.8488(5) | 0.1404(4) | 1.0726(10) | 0.078(4) |
| C14 | 0.9421(6) | 0.1289(4) | 1.0704(11) | 0.096(5) |
| C15 | 0.9936(5) | 0.1496(3) | 0.9271(12) | 0.065(4) |
| C16 | 0.9538(5) | 0.1812(3) | 0.7840(9) | 0.051(3) |
| C17 | 0.8605(5) | 0.1934(3) | 0.7858(9) | 0.050(3) |
| C21 | 0.2313(5) | 0.2874(3) | 0.8026(10) | 0.064(3) |
| C23 | 0.3926(5) | 0.0922(3) | 0.8147(9) | 0.047(3) |
| C24 | 0.3155(5) | 0.0544(3) | 0.7517(8) | 0.046(3) |
| C25 | 0.2618(5) | 0.0745(3) | 0.5700(9) | 0.048(3) |
| C27 | 0.1719(5) | 0.0544(3) | 0.2742(10) | 0.059(3) |
| C28 | 0.1270(6) | 0.0112(3) | 0.1494(10) | 0.067(3) |
| C30 | 0.1125(6) | −0.0437(3) | 0.4196(12) | 0.077(4) |
| C31 | 0.1587(5) | −0.0024(3) | 0.5544(9) | 0.058(3) |

Water molecules

| | | | | |
|---|---|---|---|---|
| O1 | 0.5321(3) | 0.06720(17) | 0.3601(6) | 0.0585(17) |
| O2 | 0.6433(3) | 0.07371(17) | 0.0243(6) | 0.0629(19) |
| O3 | 0.3895(3) | −0.00947(17) | 0.3119(6) | 0.0593(19) |

Temperature factor of the form: T = exp[−2π$^2$U], U = U(eqv) where U(eqv) = 1/3 Σ(i)Σ(j){U(ij)a(i)a(j)a(i)a(j)

EXAMPLE 10

Tablets

Specific examples of tablet formulations of an active substance of the invention comprising Form 3 ZD1839 DMSO solvate, Form 2 ZD1839 MeOH solvate or Form 1 ZD1839 polymorph, are described hereinafter.

| | mg/tablet |
|---|---|
| 100 mg Tablet | |
| Core: | |
| active substance | 100 |
| Lactose | 65.4 |
| Microcrystalline Cellulose | 20 |
| Croscarmellose Sodium | 8 |
| Polyvidone | 4 |
| Sodium Lauryl Sulphate | 0.6 |
| Magnesium Stearate | 2 |
| Coating: | |
| Methylhydroxypropylcellulose | 3 |
| Polyethylene Glycol, PEG 300 | 0.6 |
| Titanium Dioxide | 0.2 |
| 250 mg Tablet | |
| Core | |
| active substance | 250 |
| Lactose | 163.5 |
| Microcrystalline Cellulose | 50 |
| Croscarmellose Sodium | 20 |
| Polyvidone | 10 |
| Sodium Lauryl Sulphate | 1.5 |
| Magnesium Stearate | 5 |
| Coating: | |
| Methylhydroxypropylcellulose | 7.6 |
| Polyethylene Glycol, PEG 300 | 1.5 |
| Titanium Dioxide | 0.5 |

EXAMPLE 11

Aqueous Suspension

The following aqueous suspensions of Form 5 ZD1839 trihydrate may be prepared as described below:

Aqueous Suspension A:
20 mg/ml concentration Form 5 ZD1839 trihydrate in water;
0.2% Polysorbate 20;
pH 7 phosphate buffer; and
0.9% NaCl Aqueous Suspension B
10 mg/ml concentration Form 5 ZD1839 trihydrate in water;
0.2% Polysorbate 20;
pH 7 phosphate buffer; and
0.9% NaCl;

wherein % are by weight

Micronised Form 5 ZD1839 trihydrate is added to a solution of the Polysorbate in the phosphate buffer solution. The resulting mixture is mixed using a homogeniser to give a smooth suspension. The suspension is added to a solution of the sodium chloride in phosphate buffer and the suspension is mixed by stirring. Additional phosphate buffer is; added to give the required concentration of Form 5 ZD1839 trihydrate in the suspension. The pH phosphate buffer used in the suspension formulations may be prepared by dissolving monobasic sodium phosphate ($NaH_2PO_4$; 17.3 mg/ml (1.73 weight %)) and dibasic sodium phosphate ($Na_2HPO_4$; 9.36 mg/ml (0.94 weight %)) in sterile purified water.

Both suspensions are stable during prolonged storage at ambient temperature.

The invention claimed is:

1. Crystalline DMSO solvate of Form 3 ZD1839, according to the following formula I:

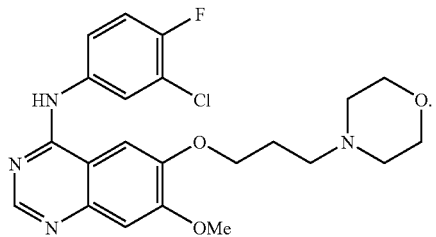

2. The solvate according to claim 1 characterised by an X-ray diffraction pattern having characterising peaks at about 8.9, 17.8, 22.6 and 23.2° on the 2θ scale.

Figure 7:
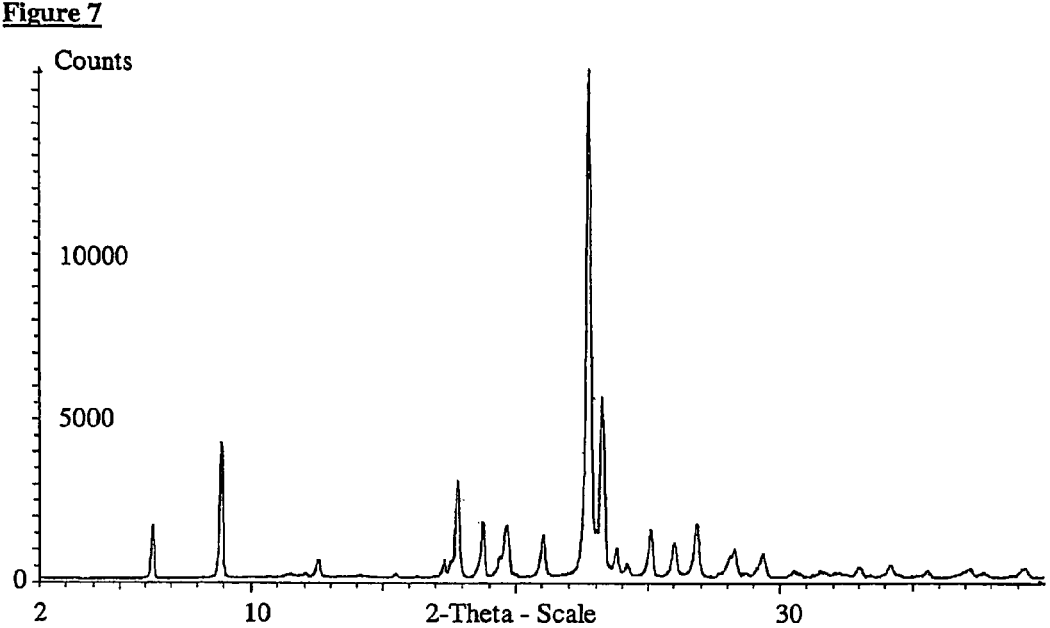
FIG. 7 shows the X-ray powder diffraction pattern for Form 3 ZD1839 DMSO solvate with the 2θ values plotted on the horizontal axis against relative line intensity values (Count) plotted on the vertical axis.

3. The solvate according to claim 1 characterised by an X-ray diffraction pattern substantially as shown in FIG. 7.

4. The solvate according to claim 1 characterised by a desolvation point in the range of about 127° C. to 132° C.

Figure 8:
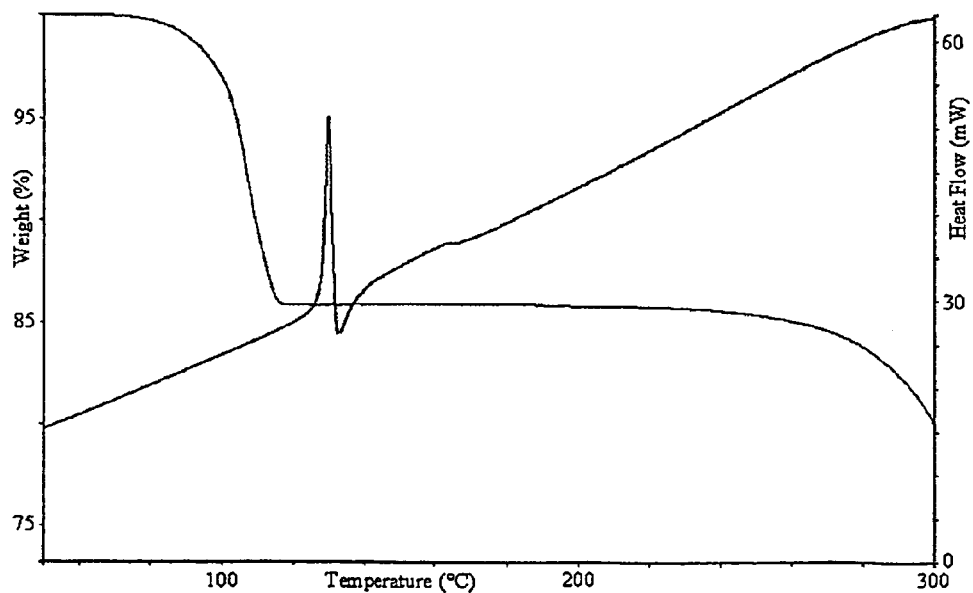
FIG. 8 shows the DSC thermogram and TGA trace for Form 3 ZD1839 DMSO solvate with temperature (° C.) plotted on the horizontal axis and endothermic heat flow (mW) and sample weight (percentage of initial weight) plotted on the two vertical axes.

5. The solvate according to claim 1 characterised by one or both of the Differential Scanning Calorimetry thermogram and Thermal Gravimetric Analysis trace substantially as shown in FIG. 8.

6. The solvate according to claim 1 characterised by a Diffuse Reflectance Infrared Fourier Transform spectrum with distinguishing peaks at about 1640, 1520, 1450, 880 and 560 $cm^{-1}$.

Figure 9:
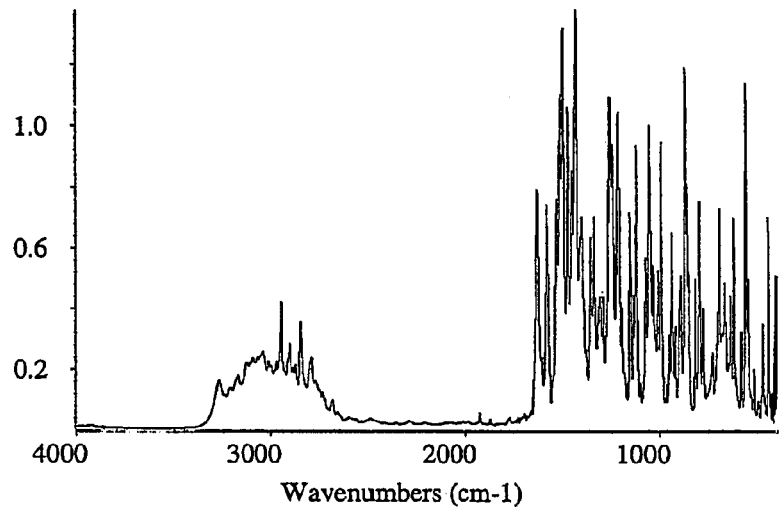
FIG. 9 shows the DRIFT spectrum for Form 3 ZD1839 DMSO solvate.
Figure 10:
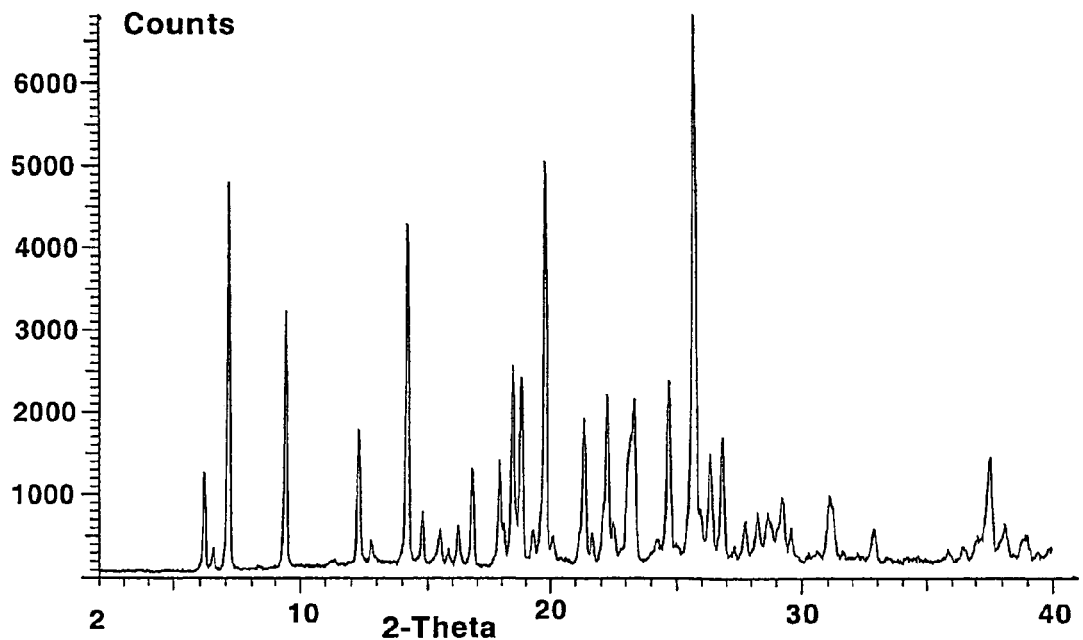
FIG. 10 shows the X-ray powder diffraction pattern for Form 5 ZD1839 trihydrate with the 2θ values plotted on the horizontal axis and the relative line intensity (Count) plotted on the vertical axis.
Figure 11:
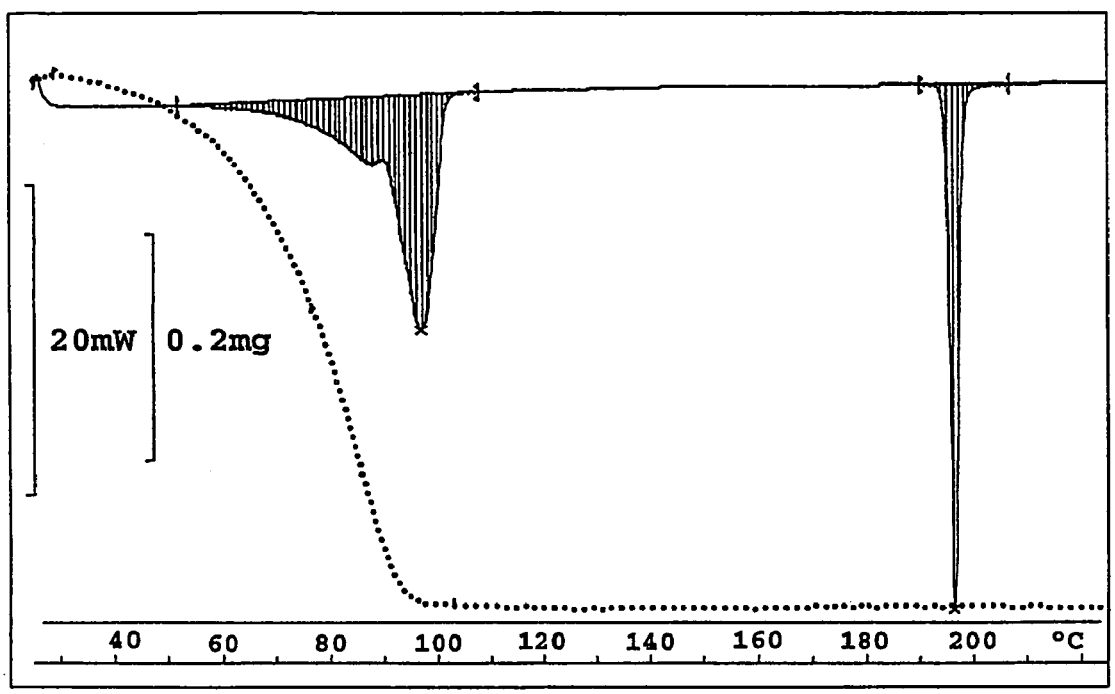
FIG. 11 shows the DSC thermogram (solid line) and TGA trace (dotted line) for Form 5 ZD1839 trihydrate with temperature (° C.) plotted on the horizontal axis and endothermic heat flow (milliwatts (mW)) and sample weight (mg) shown on the two scale bars.

7. The solvate according to claim 1 characterised by a Diffuse Reflectance Infrared Fourier Transform spectrum substantially as shown in FIG. 9.

8. The crystalline DMSP solvate of Form 3 ZD1839 according to claim 1, which is substantially free of any other ZD1839 solvate of any Form 1 ZD1839 polymorph.

9. A process for preparing a crystalline DMSO solvate of Form 3 ZD1839 according to claim 1 which comprises:—
   (a) heating a mixture of the compound 4-(3'-chloro-4'-fluoroanilino)-7-methoxy-6-(3-morpholinopropoxy) quinazoline in dimethyl sulphoxide or a solvent mixture containing dimethyl sulphoxide and a co-solvent until dissolution has occurred;
   (b) reducing the temperature of the solvent system to induce nucleation;
   (c) maintaining the mixture at a temperature below that at which nucleation has commenced; and
   (d) isolating the crystalline solid so deposited.

10. A process for the conversion of the compound of crystalline DMSO solvate of Form 3 ZD1839 according to the Formula of claim 1, to a compound of Form I ZD1839 polymorph which comprises:—
   (a) washing Form 3 ZD1839 DMSO solvate according to claim 1 with a washing solvent or solvent mixture substantially to remove dimethyl sulphoxide; and
   (b) isolating the Form 1 ZD1839 polymorph so formed.

11. The crystalline form of the compound of the Formula I according to claim 1 wherein at least 90% of the compound of Formula I is in the form of Form 3 ZD1839 DMSO solvate.

12. The crystalline form of the compound of the Formula I according to claim 1 wherein at least 95% of the compound of Formula I is in the form of Form 3 ZD1839 DMSO solvate.

13. The crystalline form of the compound of the Formula I according to claim 1 wherein at least 98% of the compound of Formula I is in the form of Form 3 ZD1839 DMSO solvate.

* * * * *

UNITED STATES PATENT AND TRADEMARK OFFICE
CERTIFICATE OF CORRECTION

| | | |
|---|---|---|
| PATENT NO. | : 7,612,077 B2 | Page 1 of 1 |
| APPLICATION NO. | : 10/505690 | |
| DATED | : November 3, 2009 | |
| INVENTOR(S) | : Gilday | |

It is certified that error appears in the above-identified patent and that said Letters Patent is hereby corrected as shown below:

On the Title page,

[*] Notice: Subject to any disclaimer, the term of this patent is extended or adjusted under 35 USC 154(b) by 809 days.

Delete the phrase "by 809 days" and insert -- by 1199 days --

Signed and Sealed this

Fourth Day of May, 2010

David J. Kappos
*Director of the United States Patent and Trademark Office*